United States Patent
Arstad et al.

(10) Patent No.: US 10,118,892 B2
(45) Date of Patent: Nov. 6, 2018

(54) COMPOUNDS AND THEIR SYNTHESIS

(71) Applicant: UCL BUSINESS PLC, London (GB)

(72) Inventors: Erik Arstad, London (GB); Kerstin Sander, London (GB); Thibault Gendron, London (GB)

(73) Assignee: UCL BUSINESS PLC, London (GB)

( * ) Notice: Subject to any disclaimer, the term of this patent is extended or adjusted under 35 U.S.C. 154(b) by 0 days.

(21) Appl. No.: 14/435,046

(22) PCT Filed: Oct. 14, 2013

(86) PCT No.: PCT/GB2013/052678
§ 371 (c)(1),
(2) Date: Apr. 10, 2015

(87) PCT Pub. No.: WO2014/057291
PCT Pub. Date: Apr. 17, 2014

(65) Prior Publication Data
US 2015/0266818 A1 Sep. 24, 2015

(30) Foreign Application Priority Data

Oct. 12, 2012 (GB) .................................. 1218352.1

(51) Int. Cl.
*C07C 381/12* (2006.01)
*C07C 17/361* (2006.01)
*C07C 25/13* (2006.01)
*C07C 45/65* (2006.01)
(Continued)

(52) U.S. Cl.
CPC ............ *C07C 381/12* (2013.01); *B01D 15/08* (2013.01); *B01J 20/22* (2013.01); *C07B 59/001* (2013.01); *C07B 59/002* (2013.01); *C07C 17/361* (2013.01); *C07C 25/13* (2013.01); *C07C 45/65* (2013.01); *C07C 47/55* (2013.01);
(Continued)

(58) Field of Classification Search
CPC ..... C07C 381/12; C07C 17/361; C07C 25/13; C07C 45/65; C07C 47/55; C07C 49/807; C07C 67/317; C07C 69/78; C07D 207/46; C07D 211/20; C07D 211/22; C07D 211/32; C07D 211/70; C07D 213/70; C07D 333/74; C07D 333/76; C07D 401/06; C07D 403/06
See application file for complete search history.

(56) References Cited

U.S. PATENT DOCUMENTS

| 4,347,187 | A | | 8/1982 | Muchowski et al. | |
|---|---|---|---|---|---|
| 4,694,029 | A | * | 9/1987 | Land | C08F 2/50 522/121 |

(Continued)

FOREIGN PATENT DOCUMENTS

| DE | 102009015413 | 9/2010 |
|---|---|---|
| EP | 0375160 | 6/1990 |

(Continued)

OTHER PUBLICATIONS

Tanabe, et al. "Oxidative arylation ny naphthalene-1, 8-diylbis (diphenylmethylium): synthetic route to triarylsulfonium salts," Chemistry Letters, vol. 39, No. 1, 2009, 56-57, XP002719266, Chemical society of Japan ISSN: 0366-7022.

Hartke K, et al. "Indole- and pyrrolesulfonium ylides," Tetrahedron, Elsevier Science Publishers, Amsterdam, NL, vol. 44, No. 11, Jan. 1, 1988, 3261-3270, XP002342692.

Bellesia F, et al. "The reaction of pyrroles with trimethylhalosilanes-dialkyl sulfoxides," Journal of Heterocyclic Chemistry, Wiley-Blackwell Publishing, Inc., US, vol. 30, No. 30, Jan. 1, 1993, 617-621, XP002342693.

(Continued)

*Primary Examiner* — Timothy R Rozof
(74) *Attorney, Agent, or Firm* — Stites & Harbison, PLLC; Terry L. Wright

(57) ABSTRACT

The present invention relates to sulfonium salts of formula (I): (I), their preparation, and utility as precursors for preparing functionalized organic compounds, wherein $R_1$ and $R_2$ are the same or different and each is independently selected from an optionally substituted aryl group, an optionally substituted alkynyl group, an optionally substituted alkenyl group, an optionally substituted alkyl group, an optionally substituted cycloalkyl group, an optionally substituted cycloalkenyl group, an optionally substituted aralkyl group, an optionally substituted arylalkenyl group, an optionally substituted heteroaryl group, an optionally substituted heterocyclyl group, an optionally substituted amine, an optionally substituted alkoxy group, an optionally substituted thioether group, an optionally substituted phosphine group, an optionally substituted boron species, an optionally substituted carbene, an organometallic moiety, and a halide, or $R_1$ and $R_2$ are joined together to form an optionally substituted sulfur-containing ring; W is a bond, an optionally substituted alkynylene group, an optionally substituted alkenylene group, and optionally substituted alkylene group, an optionally substituted heterocyclyl group, an optionally substituted aryl group or an optionally substituted heteroaryl group; $R_3$ is a moiety comprising at least one basic group, provided that when $R_3$ does not contain any carbon atoms, W is not a bond; X is an anionic species; and n is an integer selected from 1 to 5.

(I)

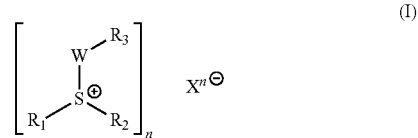

21 Claims, 15 Drawing Sheets

(51) Int. Cl.

| | | |
|---|---|---|
| C07C 47/55 | (2006.01) | |
| C07C 49/807 | (2006.01) | |
| C07C 67/317 | (2006.01) | |
| C07C 69/78 | (2006.01) | |
| C07D 207/46 | (2006.01) | |
| C07D 211/20 | (2006.01) | |
| C07D 211/22 | (2006.01) | |
| C07D 211/32 | (2006.01) | |
| C07D 211/70 | (2006.01) | |
| C07D 213/70 | (2006.01) | |
| C07D 333/74 | (2006.01) | |
| C07D 333/76 | (2006.01) | |
| C07D 401/06 | (2006.01) | |
| C07D 403/06 | (2006.01) | |
| B01D 15/08 | (2006.01) | |
| B01J 20/22 | (2006.01) | |
| C07B 59/00 | (2006.01) | |
| C07D 213/61 | (2006.01) | |

(52) U.S. Cl.
CPC .......... *C07C 49/807* (2013.01); *C07C 67/317* (2013.01); *C07C 69/78* (2013.01); *C07D 207/46* (2013.01); *C07D 211/20* (2013.01); *C07D 211/22* (2013.01); *C07D 211/32* (2013.01); *C07D 211/70* (2013.01); *C07D 213/61* (2013.01); *C07D 213/70* (2013.01); *C07D 333/74* (2013.01); *C07D 333/76* (2013.01); *C07D 401/06* (2013.01); *C07D 403/06* (2013.01)

(56) References Cited

U.S. PATENT DOCUMENTS

| | | | | |
|---|---|---|---|---|
| 4,954,416 A | * | 9/1990 | Wright | C07C 381/12 430/281.1 |
| 5,569,784 A | * | 10/1996 | Watanabe | C07C 381/12 430/270.1 |
| 5,847,218 A | | 12/1998 | Ohsawa et al. | |
| 2012/0020881 A1 | * | 1/2012 | Lehmann | A61K 51/065 424/1.69 |

FOREIGN PATENT DOCUMENTS

| | | | |
|---|---|---|---|
| EP | 2236488 | | 10/2010 |
| JP | 2008/169231 | * | 7/2008 |
| WO | 2008022319 A2 | | 2/2008 |
| WO | 2010066380 A1 | | 6/2010 |

OTHER PUBLICATIONS

A. Luttringhaus, et al. "kinetische und polarographische Untersuchungen zur Klarung ihres Wirkungs-Chemismus," Justus Liebigs Annalen Der Chemie, vol. 371, 1964, 165-196, XP002719267, Verlag Chemie GMBH.

European Patent Office, International Search Report, from corresponding International Application No. PCT/GB2013/052678, dated May 2, 2014.

Hubbard, et al. "Halo- and Azidodediazoniation of Arenediazonium Tetrafluoroborates with Trimethylsilyl Halides and Trimethylsilyl Azide and Sandmeyer-Type Bromodediazoniation with Cu(I)Br in [BMIM][PF6] Ionic Liquid," J. Org. Chem 2008, 73, 316-319.

Endo, et al. "Reaction of Benzene with Diphenyl Sulfoxides," Chem. Pharm. Bull. vol. 29, 1981, 3753-3755.

Hull, et al. "Palladium-Catalyzed Fluorination of Carbon-Hydrogen Bonds," J. Am. Chem. Soc. 2006, 128, 7134-7135.

Imazeki, et al. "Facile Method for the Preparation of Triarylsulfonium Bromides Using Grignard Reagents and Chlorotrimethylsilane as an Activator," Synthesis 2004, No. 10, 1648-1654.

Littich, et al. "Novel Strategies for Fluorine-18 Radiochemistry," Angew. Chem. Int. Ed. 2012, 51, 1106-1109.

Miller, et al. "Synthesis of 11C, 18F, 15O, and 13N Radiolabels for Positron Emission Tomography," Angew. Chem. Int. Ed. 2008, 47, 8998-9033.

Miyatake, et al. "Superacidified Reaction of Sulfides and Esters for the Direct Synthesis of Sulfonium Derivatives," J. Org. Chem. 1998, 63, 7522-7524.

Mu, et al. "F-Radiolabeling of Aromatic Compounds Using Triarylsulfonium Salts," Eur. J. Org. Chem. 1-5.

Teare, et al. "Radiosynthesis and Evaluation of [18F]Selectfluor bis(triflate)," Angew. Chem. Int. Ed. 2010, 49, 6821-6824.

* cited by examiner

COMPOUNDS AND THEIR SYNTHESIS

The present invention relates to compounds and their synthesis. In particular, though not exclusively, it concerns sulfonium salts, their preparation, and utility as precursors for preparing functionalised organic compounds.

Functionalised compounds represent a significant proportion of the drugs or related compounds currently available on the market. For example, approximately 25% of pharmaceuticals and 30% of agrochemicals contain fluorine, yet the introduction of fluorine into chemical compounds remains challenging, and there is an urgent need for more practical methods. Furthermore, corresponding radionuclides, such as fluorine-18, are also of major interest for medical imaging applications, but their radioactive nature, and the limited number of suitable reagents available, make the introduction of such radionuclides into relevant molecules a demanding and costly task.

Sulfonium salts are attractive reagents in chemical synthesis, since they are stable to the conditions typically used to isolate and purify organic molecules, and enable aromatic functionalisation in the absence of strong electron-withdrawing groups. However, their use is particularly limited in the presence of additional moieties (e.g. functional groups) in the molecule to be functionalised. This is because reactive functional groups, especially basic groups, have a propensity to hinder the formation of the sulfonium salt.

Previous methods to prepare simple sulfonium salts have involved using Grignard reactions of diphenylsulfoxide and a respective magnesium halide (Imazeki et al. *Synthesis,* 2004, 10, 1648), acid-catalysed reactions of diphenylsulfoxide with benzene (Endo et al. *Chem. Pharm. Bull.,* 1981, 29, 3753), or acid-catalysed reactions of disubstituted sulphides with esters (Miyatake et al. *J. Org. Chem.,* 1998, 63, 7522). Due to the high reactivity of the reagents employed, however, these methods are not generally compatible with many functional groups, and the chemical structures that can be accessed are therefore highly limited. Whilst it is possible to conjugate sulfonium salts to molecules bearing more complex functionalities, this approach is limited by the chemical groups that are formed during the conjugation step, as well as to the conditions that sulfonium salts will remain intact. Hence, a different procedure which is more generally applicable is required.

Mu et al. *Eur. J. Org Chem.* 2012, 5, 889, have shown that sulfonium salt precursors may be used to prepare fluoroarenes containing a limited number of functional groups. So far only simple aryl groups (containing aliphatic, aromatic and alkene side chains, in addition to alkyl, iodo and methoxy substituents) and one model peptide bearing a sulfonium salt as a leaving group have been reported. However, most biologically relevant molecules for use in the pharmaceutical and agrochemical industries possess more complex functional groups (e.g. aromatic and aliphatic amines, amidines, guanidines, aromatic and aliphatic alcohols and thiols, aldehydes, ketones, (activated) esters, sulfonic acid esters, amides, sulphonamides, ethers, thioethers, sulfoxides, sulfones, nitriles, fluorine, chlorine, bromine, etc). In presently available methods for the preparation of such compounds, protecting group methodology is used to prevent the potential interference of reactive functional moieties, thereby increasing the number of synthetic steps to reach the target compound. Also, particular functional groups, such as fluorine, which cannot be readily introduced at a late stage of the synthesis, require the use of costly functionalised fragments at an earlier stage of the synthetic route, thereby leading to an increased cost of the desired molecules.

The functionalisation of aromatic and heteroaromatic compounds is often challenging, particularly in the case of fluorination. Despite the utility of this functional group, methods available for the introduction of fluorine into aromatic and heteroaromatic compounds are rare. For instance, fluorinated compounds can be obtained from diazonium salts (Hubbarb et al. *J. Org. Chem.* 2008, 73, 316), the use of electrophilic agents such as Selectfluor® (IUPAC name: 1-(chloromethyl)-4-fluoro-1,4-diazoniabicyclo[2.2.2]octane ditetrafluoroborate) (Teare et al. *Angew. Chem. Int. Ed.* 2010, 49, 6821), or by using transition metal catalysts in conjunction with a source of electrophilic fluoride or nucleophilic fluoride (Hull et al. *J. Am. Chem. Soc.* 2006, 128, 7134). However, such methods suffer from low yields, poor selectivity, the need for high reaction temperatures or the use of microwave energy, expensive reagents, or reagents that are particularly hazardous.

In addition, current methods for fluorine-18 labelling are highly restrictive in terms of the chemical structures that can be accessed and the position in which fluorine can be introduced. For practical reasons, the vast majority of experimental tracers incorporate fluorine-18 on aliphatic side chains, despite the propensity of such moieties to undergo de-fluorination in vivo, and thus release radioactive metabolites which interfere with the diagnostic signal. In contrast, the fluorine-carbon aryl bond is highly stable, and fluorinated aryl groups are routinely employed in medicinal and agricultural chemistry to improve biological stability and to modulate pharmacological properties. This has made the development of methods for aromatic fluorination a high priority for synthetic, medicinal and agricultural chemistry.

Previous methods for introducing radioactive fluorine (fluorine-18) include the following (e.g. Miller et al. *Angew. Chem. Int. Ed.* 2008, 47, 8998, and Littich et al. *Angew. Chem. Int. Ed.* 2012, 51, 1106).

1) Electrophilic Fluorination.

Given that it is possible to produce radioactive fluorine gas, the resultant gas may be used directly or indirectly for the labelling of electron rich aromatic moieties functionalised with trialkyl tin groups. However, the method is challenging in the sense that it requires specialised cyclotron modifications, the high reactivity of fluorine gas makes handling and transport difficult, and overall the fluorination reaction is hard to control. Whilst work is continuing in this area, the use of electrophilic fluorination has declined due to the high complexity involved.

2) Nucleophilic Displacement of a Nitro Group.

The nitro leaving group can give moderate to good yields when used in nucleophilic displacement reactions, but is limited to reactions involving highly activated aromatic groups (such as 4-nitrobenzaldehyde and pyridine). High temperatures are also often required which leads to decomposition, and it can be difficult to separate unwanted by-products from the desired $^{18}$F-tracer. Very few small molecule tracers have been labelled successfully with this method, and typically microwave irradiation is required to avoid decomposition during labelling.

3) Nucleophilic Displacement of Trimethyl Ammonium Groups.

The use of trimethyl ammonium groups in nucleophilic displacement reactions has similar limitations to nitro groups. Whilst the positive charge facilitates separation of the precursor from the tracer, the synthesis of biologically active compounds containing the required trimethylphenylammonium group is challenging.

4) Iodonium Salts.

Iodonium salts enable labelling of aromatic groups without the need for other electron withdrawing moieties. However, with the exception of simple aromatics, the low stability of iodonium salts makes them difficult to purify, thereby resulting in poorly reproducible labelling yields. Despite considerable efforts to develop this chemistry, there are only a few examples so far of the use of iodinium salts to label tracers, and the method has now been largely abandoned by the field.

5) Sulfonium Salts.

The only examples illustrating the use of sulfonium salts for fluorine-18 labelling demonstrate that these salts can only be used to label simple aromatics, although fluorination can occur when the aromatic group is conjugated to a model peptide (Mu et al. *Eur. J. Org. Chem.* 2012, 5, 889). However, the necessary use of Grignard reagents, trimethylsilyl trifluoromethanesulfonate and hydrogen bromide to prepare the sulfonium salt, and the use of preparative HPLC for purification, makes this method unpractical, and severely limits its application to aromatic compounds containing essentially inert functionality.

6) Palladium Mediated Fluorination.

After intense efforts over the last decade, the first example of $^{18}$F-labelling of aromatic groups using palladium was only recently reported. The method represents a conceptual breakthrough as it involves the palladium mediated transformation of nucleophilic fluoride to an electrophilic fluorine reagent that can undergo palladium mediated cross-coupling reactions. However, the reaction relies on a highly complex ligand for palladium, and requires two freshly prepared palladium complexes (one with fluoride and the other with the tracer compound) to be combined for labelling. Moreover, it is doubtful whether the method can be applied to biologically active compounds containing amines and other common functional groups that possess the ability to coordinate to the metal catalyst. Only three examples of this method in use have been reported, each relating to highly inert structural scaffolds.

Commercial applications of radionuclide-containing tracers have enormous therapeutic and economic value. For example, positron emission tomography (PET) in conjunction with radiolabelled tracers has become the analytical standard for the diagnosis and treatment monitoring of many types of cancer, as well as cardiovascular and neurological diseases. However, the high cost and limited accessibility of radiolabelled tracers is restricting the applications of PET, and the development of practical methods for tracer production remains a major challenge for the field. With its near ideal decay properties, fluorine-18 is the only radionuclide suitable for labelling of small molecule PET tracers that has a sufficiently long half-life (110 min) to allow widespread distribution to clinical facilities without in-house cyclotron facilities. Fluorine-18 accounts for approximately 90% of all PET scans, of which the vast majority are carried out with radiolabelled glucose (FDG). The lack of efficient methods for labelling with fluorine-18 also makes the development of PET tracers exceedingly challenging as it typically requires structural modifications that impair the activity of biologically active compounds. As a result, few tracers provide a sufficient signal to justify the high cost of PET scans.

Labelling with fluorine-18 is almost exclusively limited to nucleophilic substitution of aliphatic side chains, and the preparation of prosthetic groups (aromatic and aliphatic), which can subsequently be conjugated to biological active molecules. The sequence of steps required is technically challenging, and involves highly specialised and expensive equipment.

It is an object of the present invention, therefore, to provide a general method for the functionalisation of organic moieties containing complex pendant functionality. Whilst generally applicable for the introduction of nucleophiles, such a method could be of particular interest in the preparation of biologically relevant compounds containing halides, especially fluorine. Furthermore, a more facile and efficient transformation is desired such that the product compounds may be easily prepared, isolated and purified for subsequent use.

According to the invention, there is provided a sulfonium salt according to formula (I):

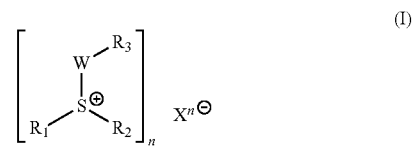

(I)

wherein
$R_1$ and $R_2$ are the same or different and each is independently selected from an optionally substituted aryl group, an optionally substituted alkynyl group, an optionally substituted alkenyl group, an optionally substituted alkyl group, an optionally substituted cycloalkyl group, an optionally substituted cycloalkenyl group, an optionally substituted aralkyl group, an optionally substituted arylalkenyl group, an optionally substituted heteroaryl group, an optionally substituted heterocyclyl group, an optionally substituted amine, an optionally substituted alkoxy group, an optionally substituted thioether group, an optionally substituted phosphine group, an optionally substituted boron species, an optionally substituted carbene, an organometallic moiety, and a halide, or $R_1$ and $R_2$ are joined together to form an optionally substituted sulfur-containing ring;
W is a bond, an optionally substituted alkynylene group, an optionally substituted alkenylene group, an optionally substituted alkylene group, an optionally substituted heterocyclyl group, an optionally substituted aryl group or an optionally substituted heteroaryl group;
$R_3$ is a moiety comprising at least one basic group, provided that when $R_3$ does not contain any carbon atoms, W is not a bond;
X is an anionic species;
and n is an integer selected from 1 to 5.

Also provided is a method of preparing a sulfonium salt according to the invention, the method comprising
i) treating a thioether according to formula (II)

(II)

with an acidic compound so as to form an acid-base adduct by virtue of the basic group of $R_3$;
ii) treating the adduct with a compound according to the formula $[(R_2)_2 I]_m^+ Z^{m-}$ or formula $[(R_1)(R_2)I]_m^+ Z^{m-}$, optionally in the presence of a catalyst, or where R₁ and R₂ are joined together to form an optionally substituted sulfur-containing ring in formula (I), treating an adduct of formula (II) formed in step (i) in which R₁ contains at least one unsaturated bond, with an acid or electrophilic species so as to cause formation the optionally substituted sulfur-containing ring; and iii) recovering the product sulfonium salt, wherein $R_1$, $R_2$, W and $R_3$ are as defined in relation to the sulfonium salt of formula (I), Z is an anionic species, and m is an integer selected from 1 to 5.

In addition, there is provided a method of preparing a compound according to formula (III):

the method comprising i) treating a sulfonium salt according to formula (I) with a species capable of generating a nucleophile Y, optionally in the presence of a base and/or chelating agent; and ii) recovering the compound according to formula (III), wherein $R_3$ and W are as defined in relation to the sulfonium salt of formula (I).

Surprisingly, it has been found that it is possible to prepare a range of sulfonium salts containing unprotected basic functionalities. In addition, it has been advantageously discovered that such sulfonium salts undergo facile reactions with nucleophiles under gentle heating (e.g. less than 50° C.) or ambient conditions (particularly where W in W—$R_3$ is represented by aryl (e.g. phenyl) or heteroaryl (e.g. pyridine), optionally substituted with electron withdrawing groups, and/or wherein $R_3$ is bound to W by way of an electron withdrawing group such as a carbonyl group).

It will be understood that, in the method of preparing a compound of formula (III), the nucleophile Y becomes attached to W (or $R_3$, when W is a bond) at the same position to which the $S^+$ is attached in the sulfonium salt of formula (I).

Furthermore, there is also provided a solid phase adsorbent comprising a sulfonium salt according to formula (I).

There is also provided a general method for the nucleophilic substitution of a sulfonium salt having the formula $[SR_aR_bR_c]^+T^-$, the method comprising: (i) reacting a compound comprising a nucleophilic group Q with the sulfonium salt at a temperature below 80° C.; and (ii) recovering the product $R_cQ$ from the mixture of $R_cQ$ and $SR_aR_b$, wherein $R_a$, $R_b$, and $R_c$ may be the same or different and comprise chemical groups comprising at least two atoms having a covalent bond therebetween, and T is a counterion. It is preferable that this method is carried out at room pressure and at a temperature of less than 60° C., for example at less than 55° C., less than 50° C., or less than 45° C. Most preferably, the reaction is performed at room temperature.

The sulfonium salts of the present invention have been found to be useful precursors in the preparation of functionalised organic compounds. In particular, the salts are produced in a single step procedure which tolerates the presence of basic functionalities. This means that the required nucleophile may be introduced at a late stage of the synthesis, which has important implications for the synthesis of compounds containing functionalities that are typically difficult to introduce, in particular fluorine, and radioactive isotopes thereof.

The term '$C_{x-y}$ alkyl' as used herein refers to a linear or branched saturated hydrocarbon group containing from x to y carbon atoms. For example, $C_{1-16}$ alkyl refers to a linear or branched saturated hydrocarbon group containing from 1 to 16 carbon atoms. Examples of $C_{1-16}$ alkyl groups include methyl, ethyl, n-propyl, isopropyl, n-butyl, isobutyl, sec-butyl, tert-butyl, n-pentyl, isopentyl, neopentyl, hexyl, isohexyl, 1,1-dimethylbutyl, 2,2-dimethylbutyl, 3,3-dimethylbutyl, 2-ethylbutyl, heptyl, octyl, nonyl, and decyl.

The term '$C_{x-y}$ alkylene' as used herein refers to a divalent hydrocarbon group obtained by removing one hydrogen atom from '$C_{x-y}$ alkyl' above. Examples of $C_{1-16}$ alkylene groups include methylene, ethylene and propylene.

The term '$C_{x-y}$ alkenyl' as used herein refers to a linear or branched hydrocarbon group containing one or more carbon-carbon double bonds and having from x to y carbon atoms. Examples of $C_{2-16}$ alkenyl groups include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, and 1-octenyl.

The term '$C_{x-y}$ alkenylene' as used herein refers to a divalent hydrocarbon group obtained by removing one hydrogen atom from '$C_{x-y}$ alkenyl' above (e.g. —CH=CH— or >C=CH₂). Examples of $C_{2-16}$ alkenylene groups include vinylene and propenylene.

The term '$C_{x-y}$ alkynyl' as used herein refers to a divalent hydrocarbon group containing one or more carbon-carbon triple bonds and having from x to y carbon atoms. Examples of $C_{2-16}$ alkynyl groups include ethynyl, propynyl, butynyl and pentynyl.

The term '$C_{x-y}$ alkynylene' as used herein refers to a divalent hydrocarbon group obtained by removing one hydrogen atom from '$C_{x-y}$ alkynyl' above (e.g. —C≡C—). Examples of $C_{2-16}$ alkynylene groups include propynylene, butynylene and pentynylene.

The term '$C_{x-y}$ alkoxy' as used herein refers to an —O—$C_{x-y}$ alkyl group wherein $C_{x-y}$ alkyl is as defined herein. Examples of $C_{1-16}$ alkoxy groups include methoxy, ethoxy, propoxy, butoxy, pentoxy and hexoxy.

The term '$C_{x-y}$ cycloalkyl' as used herein refers to a saturated monocyclic hydrocarbon ring of x to y carbon atoms. For example, $C_{3-16}$ cycloalkyl refers to a saturated monocyclic hydrocarbon ring of 3 to 16 carbon atoms. Examples of $C_{3-16}$ cycloalkyl groups include cyclopropyl, cyclobutyl, cyclopentyl, cyclohexyl, cycloheptyl and cyclooctyl.

The term '$C_{x-y}$ cycloalkenyl' as used herein refers to a monocyclic or bicyclic hydrocarbon ring containing one or more carbon-carbon double bonds of x to y carbon atoms. For example, $C_{3-16}$ cycloalkenyl refers to an unsaturated monocyclic or bicyclic hydrocarbon ring of 3 to 16 carbon atoms. Examples of $C_{3-16}$ cycloalkenyl groups include 2-cyclopenten-1-yl, 3-cyclopenten-1-yl, 2-cyclohexen-1-yl, 3-cyclohexen-1-yl, fulvenyl, and norbornenyl.

The term '$C_{x-y}$ aralkyl' as used herein refers to a linear or branched saturated hydrocarbon group linked to an aryl group containing from x to y carbon atoms in total. Examples of $C_{7-16}$ aralkyl groups include benzyl, phenethyl, naphthylmethyl, and biphenylylmethyl.

The term '$C_{x-y}$ arylalkenyl' as used herein refers to a linear or branched hydrocarbon group containing one or more carbon-carbon double bonds linked to an aryl group and having from x to y carbon atoms in total. Examples of $C_{8-16}$ arylalkenyl groups include styryl.

The term 'halogen' as used herein refers to a fluorine, chlorine, bromine or iodine atom, and any radioactive isotope thereof, including fluorine-18, iodine-123, iodine-124, iodine-125, iodine-131, and astatine-211, unless otherwise specified.

The term 'halo$C_{1-6}$ alkyl' as used herein refers to a $C_{1-6}$ alkyl group as defined herein wherein at least one hydrogen atom is replaced with halogen. Examples of such groups include fluoroethyl, trifluoromethyl and trifluoroethyl.

The term 'aryl' as used herein refers to a monocyclic, bicyclic, or tricyclic hydrocarbon ring wherein at least one ring is aromatic. Examples of $C_{6-16}$ groups include phenyl, naphthyl, tetrahydronaphthalenyl, anthryl, phenanthryl, acenaphthylenyl, biphenylyl, anthracenyl, phenanthrenyl, phenalenyl, and carbazolyl.

The term 'heteroaryl' as used herein refers to a 5-6 membered monocyclic aromatic or a fused 8-16 membered bicyclic or tricyclic aromatic ring in which the monocyclic, bicyclic or tricyclic rings contain 1 to 4 heteroatoms selected from oxygen, nitrogen, sulphur, and phosphorus. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, and tetrazinyl. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl imidazopyridyl, and purinyl. Examples of such tricyclic rings carbazolyl, carbolenyl, xanthenyl, and dibenzothiophenyl The term 'heterocyclyl' refers to a 4-7 membered monocyclic ring or a fused 8-16 membered bicyclic or tricyclic rings which may be saturated or partially unsaturated, in which the monocyclic, bicyclic, or tricyclic rings contain 1 to 4 heteroatoms selected from oxygen, nitrogen, silicon or sulphur. Examples of such monocyclic rings include aziridinyl, oxiranyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, xanthinyl, quinuclidinyl, 2,3,4,5-tetrahydro-1H-3-benzazepine and tetrahydroisoquinolinyl.

The term 'N-containing-heterocyclyl' refers to a ring containing at least one nitrogen atom and selected from among the 'heterocyclyl' groups mentioned above. Preferred examples of such rings include pyrrolidinyl, aziridinyl, azetidinyl, piperidinyl, piperazinyl, morpholinyl, thiomorpholinyl, and azepanyl.

The term 'N-containing-heteroaryl' refers to a ring containing at least one nitrogen atom and selected from among the 'heteroaryl' groups mentioned above. Preferred examples of such rings include pyrrolyl, pyrazolyl, pyrimidyl, pyridazinyl, pyrazinyl, pyridyl, and indolyl.

The term 'amine' refers to an organonitrogen compound with the connectivity —$N(R_4)_2$, where $R_4$ is as defined below.

The term 'thioether' refers to an organosulfur compound with the connectivity —$SR_5$, where $R_5$ is as defined below.

The term 'phosphine' refers to organophosphorus compound with the connectivity —$P(R_6)_2$, where $R_6$ is as defined below.

The groups $R_4$ and $R_6$ may be independently selected from hydrogen, alkyl, aryl, heterocyclyl, heteroaryl, or cycloalkyl, or may be joined together to form, together with the nitrogen or sulfur atoms, respectively, an N-containing-heterocyclyl group or an S-containing-heterocyclyl group. The S-containing-heterocyclyl group may be analogous to the N-containing-heterocyclyl group defined in relation to $R_1$ and $R_2$, except with a sulfur atom in place of the nitrogen atom. The alkyl, aryl, heterocyclyl, heteroaryl, and cycloalkyl groups may be defined in accordance with the definitions of $R_1$ and $R_2$.

The group $R_5$ may be selected from hydrogen, alkyl, aryl, heterocyclyl, heteroaryl, or cycloalkyl. The alkyl, aryl, heterocyclyl, heteroaryl, and cycloalkyl groups may be defined in accordance with the definitions of $R_1$ and $R_2$.

The term 'boron species' refers to an organic compound containing boron, such as a borane (e.g. —$BH_2$), perhaloborane (e.g. —$BF_2$) boronic acid (e.g. —$B(OH)_2$), borinic acid (—B(R)OH), borinate ester (—B(R)OR), or boronate ester (e.g. —$B(OR)_2$). In the case of a borinic acid, borinate ester, or boronate ester, R may be a substituent as defined below.

The term 'carbene' refers to a molecule containing a neutral carbon atom with a valence of two and two unshared valence electrons. The general formula is $R_xR_yC$:, although the carbon may form a double bond to another group. Examples of suitable carbene groups include 1,3-bis(2,4,6-trimethylphenyl)imidazole and 1,3-bis(2,4,6-trimethylphenyl)dihydroimidazole.

The term 'organometallic moiety' refers to chemical compounds containing bonds between carbon and a metal. Such moieties usually contain metal-element bonds of a largely covalent character. Suitable examples of organometallic moieties include complexes containing iron, ruthenium, palladium, rhodium, platinum, zirconium, zinc, cobalt and copper as the metal centre. Suitable ligands for the organometallic moiety include cyclopentadienyl, allyl, carbonyl, triphenylphospinyl, and acetylacetonatyl. Thus, example organometallic complexes include ferrocenyl. An organometallic moiety may be optionally substituted.

The term 'hydrocarbon' refers to an optionally substituted $C_{1-6}$ alkyl, $C_{2-6}$ alkenyl, $C_{2-6}$ alkynyl, $C_{3-7}$ cycloalkyl, $C_{6-14}$ aryl, or $C_{7-16}$ aralkyl group.

Each symbol in formula (I) is described in detail in the following.

$R_1$ and $R_2$ are the same or different and each is independently selected from an optionally substituted aryl group, an optionally substituted alkynyl group, an optionally substituted alkenyl group, an optionally substituted alkyl group, an optionally substituted cycloalkyl group, an optionally substituted cycloalkenyl group, an optionally substituted aralkyl group, an optionally substituted arylalkenyl group, optionally substituted heteroaryl group, and an optionally substituted heterocyclyl group, an optionally substituted amine, an optionally substituted alkoxy group, an optionally substituted thioether, an optionally substituted phosphine, an optionally substituted boron species, an optionally substituted carbene, an organometallic moiety, and a halide, or $R_1$ and $R_2$ are joined together to form an optionally substituted sulfur-containing ring.

In particular, $R_1$ and $R_2$ may be independently selected, for example, from a $C_{6-16}$ aryl group, a $C_{2-16}$ alkynyl group, $C_{2-16}$ alkenyl group, $C_{1-16}$ alkyl group, a $C_{3-16}$ cycloalkyl group, a $C_{3-16}$ cycloalkenyl group, a $C_{7-16}$ aralkyl group, a $C_{8-16}$ arylalkenyl group, a 5- to 16-membered hetereoaryl group, a 4- to 16-membered heterocyclyl group, a $C_{2-6}$ alkynylene group, a $C_{1-6}$ alkyl or $C_{6-16}$ aryl amine, a $C_{1-16}$ alkoxy group, a $C_{1-16}$ thioether group, a $C_{1-16}$ phosphine group, a boronate ester, a carbene, an organometallic moiety linked to the sulfur atom via a ligand, each optionally substituted. Alternatively, $R_1$ and $R_2$ may be joined together to form an optionally substituted 3- to 7-membered sulfur-containing ring.

In embodiments in which $R_t$ and/or $R_2$ are, or comprise, $C_{6-16}$ aryl, said $C_{6-16}$ aryl group may be selected from, for example, phenyl, 1-naphthyl, and 2-naphthyl, anthracenyl, phenanthrenyl, and phenalenyl.

In embodiments in which $R_1$ and/or $R_2$ are, or comprise, $C_{2-16}$ alkynyl, said $C_{2-16}$ alkynyl group may be selected from, for example, ethynyl, propynyl, butynyl and pentynyl.

In embodiments in which $R_1$ and/or $R_2$ are, or comprise, $C_{2-16}$ alkenyl, said $C_{2-16}$ alkenyl may be selected from, for example, ethenyl, propenyl, butenyl, pentenyl, hexenyl, heptenyl, and octenyl.

In embodiments in which $R_1$ and/or $R_2$ are, or comprise, $C_{1-16}$ alkyl, said $C_{1-16}$ alkyl group may be selected from, for example, methyl, ethyl, propyl, isopropyl, butyl, isobutyl, sec-butyl, tert-butyl, pentyl, isopentyl, neopentyl, 1-ethyl-propyl, hexyl, isohexyl, 1,1-dimethylbutyl, 2,2-dimethylbutyl, 3,3-dimethylbutyl, 2-ethylbutyl, heptyl, octyl, nonyl, and decyl. In certain embodiments, a $C_{1-6}$ alkyl group is preferable.

In embodiments in which $R_1$ and/or $R_2$ are, or comprise, $C_{3-16}$ cycloalkyl, said $C_{3-16}$ cycloalkyl group may be selected from, for example, cyclopropyl, cyclobutyl, cyclopentyl, and cyclohexyl.

In embodiments in which $R_1$ and/or $R_2$ are, or comprise, $C_{3-16}$ cycloalkenyl, said $C_{3-16}$ cycloalkenyl group may be selected from, for example, 2-cyclopenten-1-yl, 3-cyclopenten-1-yl, 2-cyclohexen-1-yl, and 3-cyclohexen-1-yl.

In embodiments in which $R_1$ and/or $R_2$ are, or comprise, $C_{7-16}$ aralkyl, said $C_{7-16}$ aralkyl group may be selected from, for example, benzyl, phenethyl, naphthylmethyl, and biphenylylmethyl.

In embodiments in which $R_1$ and/or $R_2$ are, or comprise, $C_{8-16}$ arylalkenyl, said $C_{8-16}$ arylalkenyl group may be styryl.

In embodiments in which $R_1$ and/or $R_2$ are, or comprise, heteroaryl, said heteroaryl group may be a 5-6 membered monocyclic aromatic or a fused 8-16 membered bicyclic or tricyclic aromatic ring in which the monocyclic, bicyclic or tricyclic rings contain 1 to 4 heteroatoms selected from oxygen, nitrogen and sulphur. Preferable examples of such monocyclic aromatic rings include thienyl, furyl, pyrrolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazole and tetrazole. Preferable examples of such bicyclic aromatic rings include quinolinyl, quinazolinyl, quinoxalinyl, naphthyridinyl, indolyl, azaindolyl, indolizinyl, indazolyl, pyrrolopyridinyl, furopyridinyl, benzofuranyl, benzothienyl, benzoimidazolyl, benzoxazolyl, benzothiazolyl, benzoxadiazolyl, benzothiadiazolyl and imidazopyridyl. Preferable examples of such tricyclic aromatic rings include carbazolyl, carbolenyl, xanthenyl, and dibenzothiophenyl.

In embodiments in which $R_1$ and/or $R_2$ are, or comprise, heterocyclyl, said heterocyclyl group may be a 4-7 membered monocyclic ring or a fused 8-16 membered bicyclic or tricyclic ring which may be saturated or partially unsaturated, in which the monocyclic or bicyclic rings contain 1 to 4 heteroatoms selected from oxygen, nitrogen, silicon, sulphur, or phosphorus. Preferable examples of such monocyclic rings include pyrrolidinyl, pyrazolidinyl, oxazolidinyl, piperidinyl, piperazinyl, morpholinyl, thiomorpholinyl, thiazolidinyl, oxiranyl, dioxanyl, oxathiolanyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, and tetrahydrothiopyranyl. Preferable examples of such bicyclic rings include indolinyl, benzopyranyl, quinuclidinyl, xanthinyl, 2,3,4,5-tetrahydro-1H-3-benzazepine and tetrahydroisoquinolinyl.

In embodiments in which $R_1$ and/or $R_2$ are, or comprise, $C_{1-6}$ alkyl or $C_{6-16}$ aryl amine, said amine may be mono- or di-substituted with an alkyl or aryl group selected from, methyl, ethyl, propyl, butyl, pentyl and phenyl.

In embodiments in which $R_1$ and/or $R_2$ are, or comprise, $C_{1-16}$ alkoxy, said $C_{1-16}$ alkoxy may be selected from methoxy, ethoxy, propoxy, butoxy, pentoxy and hexoxy.

In embodiments in which $R_1$ and/or $R_2$ are, or comprise, $C_{1-16}$ thioether, said $C_{1-16}$ thioether may be selected from thiomethyl, thioethyl, thiopropyl, thiobutyl, and thiopentyl.

In embodiments in which $R_1$ and/or $R_2$ are, or comprise, $C_{1-16}$ phosphine, said $C_{1-16}$ phosphine may be mono- or di-substituted with an alkyl or arly group selected from, methyl, ethyl, propyl, butyl, pentyl and phenyl.

In embodiments in which $R_1$ and/or $R_2$ are, or comprise, boronate ester, said boronate ester may be a $C_{1-6}$ alkyl or $C_{6-14}$ aryl boronate ester.

In embodiments in which $R_1$ and/or $R_2$ are, or comprise, a carbene, said carbene may be a $C_{1-6}$ alkyl carbene, a $C_{6-16}$ aryl carbene, or a $C_{6-22}$ N-heterocyclic-carbene. Examples of suitable carbene groups include 1,3-bis(2,4,6-trimethylphenyl)imidazole and 1,3-bis(2,4,6-trimethylphenyl)dihydroimidazole.

In embodiments in which $R_1$ and/or $R_2$ are, or comprise, an organometallic moiety, the sulfur atom of the sulfonium salt may be covalently linked to a ligand of the organometallic moiety. A suitable example of such an organometallic complex is ferrocene.

Each of the optionally substituted aryl, optionally substituted alkynyl, optionally substituted alkenyl, optionally substituted alkyl, optionally substituted cycloalkyl, optionally substituted cycloalkenyl, optionally substituted aralkyl, optionally substituted arylalkenyl, optionally substituted heteroaryl, optionally substituted heterocyclyl, optionally substituted amine, optionally substituted alkoxy, optionally substituted thioether, optionally substituted phosphine, and optionally substituted carbene groups, the optionally substituted boron species, the organometallic moiety, or the optionally substituted sulfur-containing ring where $R_1$ and $R_2$ are joined together, may be substituted by:

(1) a group selected from -J-aryl, -J-heteroaryl, -J-heterocyclyl and -J-$C_{3-8}$ cycloalkyl, wherein J represents a bond or $C_{1-8}$ alkylene, and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), $C_{1-6}$ alkenyl (preferably propenyl), $C_{1-6}$ alkynyl (preferably ethynyl or propynyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl, including ketones and derivatives thereof such as ketals and hemiketals, (preferably acetyl), carboxyl, $C_{1-6}$ carbonyl, including aldehydes (e.g. formyl) and derivatives thereof such as acetals and hemiacetals, $C_{1-6}$ alkoxy-carbonyl, including esters, succinimide esters, alkyl or aryl amide, alkyl or aryl carbamate, alkyl or aryl amine, aminooxide, hydroxylamine, an amino acid, azide, alkyl or aryl azine, alkyl or aryl aziridine, alkyl or aryl azoxy, alkyl or aryl azo, borane, isonitrile, isocynates, isothiocyantes, $C_{1-8}$ lactone, nitro, alkyl or aryl nitrone, alkyl or aryl phosphine, alkyl or aryl phosphonate, alkyl or aryl silane, alkyl or aryl sulfone, alkyl or aryl sulfoxide, alkyl or aryl thioether, alkyl or aryl enol ether, alkyl or aryl enol thioether, alkyl or aryl epoxide, alkyl or aryl hydrazine, sulfonic acid and salts thereof, alkyl or aryl imide, alkyl or aryl imine, alkyl or aryl amidine, alkyl or aryl guanidine, alkyl or aryl sulphonamide, sulfonesters, alkyl or aryl imide, alkyl or aryl urea, alkyl or aryl thiourea, alkyl or aryl vinylic ethers and trialkyltin. Any of the alkyl or aryl groups mentioned in relation to the substituents for $R_1$ and $R_2$ may be a $C_{1-6}$ alkyl group or a $C_{6-14}$ aryl group.

In another embodiment, $R_1$ and $R_2$ may be joined together to form an optionally substituted sulfur-containing ring, preferably a 4- to 7-membered sulfur-containing ring. Such a ring may then be part of a larger ring system, including bicyclic and tricyclic ring systems. $R_1$ may be directly linked to $R_2$ by way of a covalent bound, or may be linked by means of a linking group comprising 1 to 3 atoms independently selected from carbon, nitrogen, oxygen, sulfur, and phosphorus. For example, $R_1$ and $R_2$ may form, with the sulfur atom of the sulfonium salt, a benzothiophene ring or a dibenzothiophene ring.

Preferably, $R_1$ and $R_2$ are each independently selected from an optionally substituted aryl group, an optionally substituted alkenyl group, an optionally substituted alkyl group, an optionally substituted heteroaryl group and an optionally substituted heterocyclyl group. More preferably, $R_1$ and $R_2$ are both an optionally substituted aryl group, an optionally substituted alkenyl group, or an optionally substituted heteroaryl group. Even more preferably, $R_1$ and $R_2$ are each independently selected from an optionally substituted aryl group and an optionally substituted heteroaryl group.

Alternatively, at least one of $R_1$ and $R_2$ is a $C_{6-14}$ aryl group. Most preferably, $R_1$ and $R_2$ are both an optionally substituted $C_{6-14}$ aryl group.

In another preferred embodiment, $R_1$ and/or $R_2$ are substituted with at least one electron donating group. Suitable examples of electron donating groups include $C_{1-6}$ alkoxy (preferably methoxy), $C_{1-6}$ alkylthioether, $C_{1-6}$ dialkylamino, $C_{1-6}$ alkoxycarbonyl (i.e. —O—C(O)—$C_{1-6}$ alkyl), and acetamides of the formula —NH—C(O)—$C_{1-6}$ alkyl, each optionally substituted with 1 to 3 halogen atoms. Surprisingly, when $R_1$ and/or $R_2$ contain such electron donating groups, nucleophilic substitution is preferentially directed to $R_3$.

In formula (I), W is a bond, an optionally substituted alkynylene group, an optionally substituted alkenylene group, an optionally substituted alkylene group, an optionally substituted heterocyclyl group, an optionally substituted aryl group or an optionally substituted heteroaryl group.

Suitable substituents for the optionally substituted alkynylene group, optionally substituted alkenylene group, optionally substituted alkylene group, optionally substituted heterocyclyl group, optionally substituted aryl group or optionally substituted heteroaryl group of W include those exemplified as substituents in relation to $R_1$ and $R_2$.

Preferably, W is a bond, an optionally substituted alkylene group, an optionally substituted heterocyclyl group, an optionally substituted aryl group, or an optionally substituted heteroaryl group. More preferably, W is a bond, an optionally substituted aryl group, or an optionally substituted heteroaryl group. Alternatively, W is preferably an optionally substituted alkylene group, an optionally substituted heterocyclyl group, an optionally substituted aryl group, or an optionally substituted heteroaryl group.

More preferably, W is an optionally substituted aryl group or an optionally substituted heteroaryl group.

In particular, the optionally substituted aryl group may be a $C_{6-14}$ aryl group, which may be selected from, for example, phenyl, naphthyl, and biphenylyl. The optionally substituted heteroaryl group may be, for example, a 5-6 membered monocyclic aromatic or a fused 8-16 membered bicyclic or tricyclic aromatic ring in which the monocyclic, bicyclic or tricyclic rings contain 1 to 4 heteroatoms selected from oxygen, nitrogen, sulphur, and phosphorus. Preferable examples of such monocyclic aromatic rings include thienyl, furyl, pyrrolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, and pyridyl. Preferable examples of such bicyclic aromatic rings include quinolinyl, quinazolinyl, quinoxalinyl, naphthyridinyl, indolyl, azaindolyl, indolizinyl, indazolyl, pyrrolopyridinyl, furopyridinyl, benzofuranyl, benzothienyl, benzoimidazolyl, benzoxazolyl, benzothiazolyl, benzoxadiazolyl, benzothiadiazolyl and imidazopyridyl. Preferable examples of such tricyclic aromatic rings include carbazolyl, carbolenyl, xanthenyl, and dibenzothiophenyl.

Preferably, W is an optionally substituted $C_{6-14}$ aryl group.

In formula (I), $R_3$ is a moiety comprising at least one basic group. Given that the sulfonium salts have such widespread utility in the halogenation of organic compounds, and may be used to produce diagnostic radiolabelled tracer compounds, the structural nature of this moiety is not limited in any way, except in that it contains a basic group. In many embodiments, $R_3$ will also contain at least one (usually several) carbon atoms, hydrogen atoms and, in several instances, nitrogen and/or oxygen and/or sulfur atoms. In a preferred aspect, $R_3$ is bound to W by way of an electron withdrawing group such as a carbonyl group, e.g. —W—C(O)—.

It will be understood that in the grouping W—$R_3$, W may contain a basic group. In such cases, the grouping W—$R_3$ will contain more than one basic group.

In particular, W—$R_3$ may be defined as a group capable of binding to a biological target. Such a target may be any biochemical motif, for example formed from a peptide, saccharide nucleotide, or lipid structure, which is susceptible of recognition and non-covalent binding by an endogenous or exogenous binding partner. Suitable biological targets include, for example, receptors for endogenous ligands, antigens associated with particular tissue or cell types, enzymes, reuptake transporters, efflux transporters, metabolic co-factors, signalling molecules, RNA, DNA, and protein aggregation mechanisms.

As exemplary biological targets, the following can be mentioned: G-protein coupled receptors (dopamine, serotonine, histamine, norepinephrine, stereoid, cannabinoid, muscarinic, nicotinic, and pheromone receptors), ion-channels (VGSCs, NMDAR, AMPA receptors, kainate receptors, potassium channels, hERG, chlorine channels, nicotinic, GABA), transporters (amino acids, Glut, nucleotides, neurotransmitter reuptake transporters), efflux pumps (P-gp, MRPs, BCRP), enzymes (caspases, metabolic enzymes, COX), and nuclear receptors (FXR, PPAR), as well as protein aggregates (amyloid peptides and tau protein).

Also, bearing in mind that the sulfonium salts of the invention may be used to functionalise known pharmacologically active agents (e.g. pharmaceutical agents, herbicides, pesticides, insecticides, and plant hormone mimetics), with either naturally occurring nucleophiles, including halides or any corresponding radionuclide variants thereof, the moiety $R_3$ may be a fragment (i.e. a residue of the known agent which excludes an aryl or heteroaryl group which, it will be understood, corresponds with W of formula (I)) of a known pharmacologically active agent, or a prodrug or structural analogue thereof.

Preferably, W—$R_3$ corresponds with a biologically active agent, preferably a known biologically active agent which is absent a required halogen atom, or represents a prodrug or structural analogue of a known biologically active agent. Such biologically active agents may be small molecule organic species (e.g. having a molecular weight of 2500 g/mol or less, such as 1000 g/mol or less) or larger, for example, peptidic species, including antibodies. Preferably, the biologically active agent is a small molecule organic species.

In an embodiment, a biologically active agent is an active ingredient of a medicinal product which is the subject of a marketing authorisation or marketing authorisation application issued by or considered by the medicines regulatory authorities of Europe, the United States of America or Japan.

Specific examples of biologically active agents or prodrugs which may be functionalised using the sulfonium salts of the present invention include, but are by no means limited to, terfenadine (IUPAC name: (RS)-1-(4-tert-butylphenyl)-4-{4-[hydroxy(diphenyl)methyl]piperidin-1-yl}-butan-1-ol), fexofenadine (IUPAC name: (RS)-2-[4-[1-Hydroxy-4-[4-(hydroxy-diphenyl-methyl)-1-piperidyl]butyl]phenyl]-2-methyl-propanoic acid), hydroxyzine (IUPAC name: (±)-2-(2-{4-[(4-chlorophenyl)-phenylmethyl]piperazin-1-yl}ethoxy)ethanol), cetirizine (IUPAC name: (±)-[2-[4-[(4-chlorophenyl)phenylmethyl]-1-piperazinyl]ethoxy]acetic acid), cyclizine (IUPAC name: 1-benzhydryl-4-methyl-piperazine), buclizine (IUPAC name: (RS)-1-[(4-chlorophenyl)-phenyl-methyl]-4-[(4-tert-butylphenyl)methyl]piperazine), meclozine (IUPAC name: (RS)-1-[(4-chlorophenyl)(phenyl)methyl]-4-(3-methylbenzyl) piperazine).

Other specific examples of compounds of formula (III) of particular interest include the following (examples shown following fluorination).

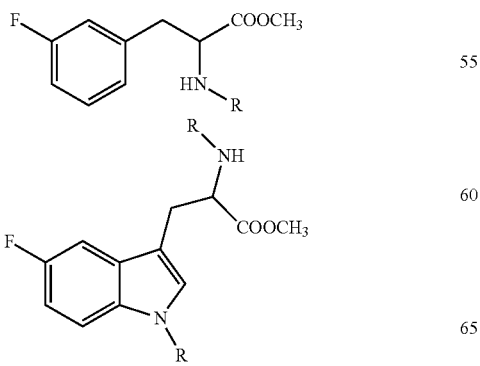

-continued

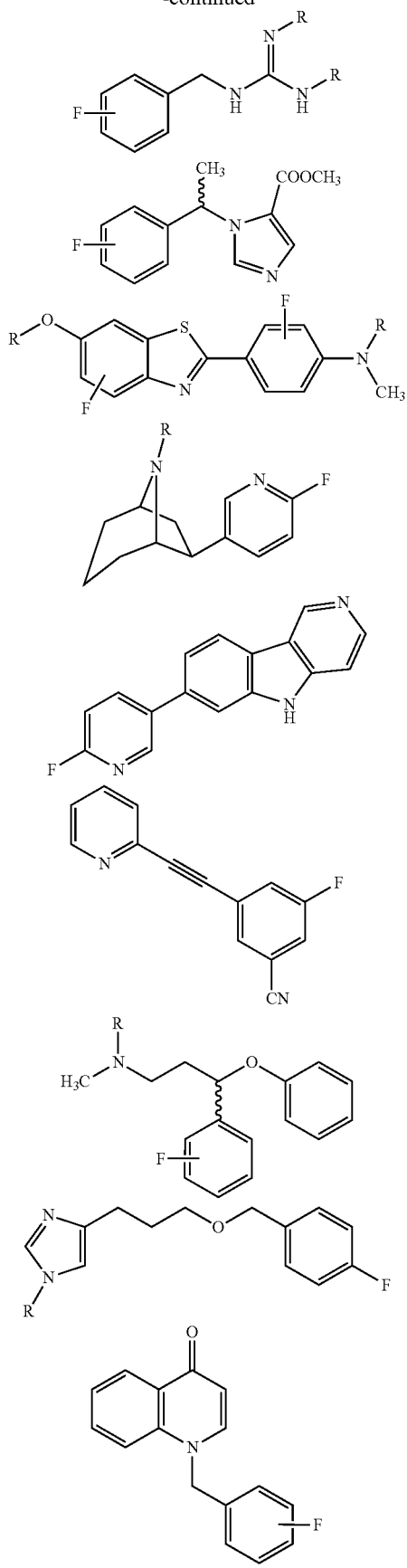

-continued

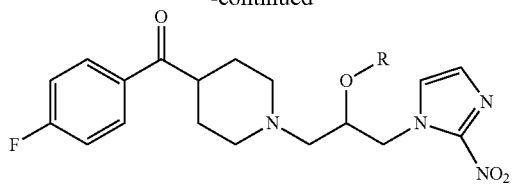

F = ¹⁸,¹⁹F/R = H, protecting group

The basic group for $R_3$ may be a Brønsted base and/or a Lewis base. A Brønsted base is defined in this context as a species with the ability to gain, or accept, a hydrogen cation (i.e. a proton). Suitable examples of Brønsted bases include amines, amidines, guanidines, hydroxyamines, imines and oxyimines, as well as a range of heteroaryl and heterocyclic groups (bicyclic, tricyclic, fused and bridged ring systems) containing 1-4 nitrogen atoms (e.g. anilines).

A Lewis base is defined in this context as any species that can donate a pair of electrons to a Lewis acid to form a Lewis adduct. Thus, a Lewis base is a molecular species where the highest occupied molecular orbital (HOMO) is highly localized. Typical Lewis bases are conventional amines such as alkyl amines. Other common Lewis bases include pyridine and its derivatives. Some of the main classes of Lewis bases are (i) amines of the formula $NH_{3-x}R_x$ where R=alkyl or aryl, as defined above for $C_{x-y}$ alkyl and $C_{x-y}$ aryl, or an N-containing-heterocyclyl group including those related to pyridine and its derivatives; (ii) phosphines of the formula $PR_{3-x}R_x$, where R=alkyl, A=aryl, as defined above for $C_{x-y}$ alkyl and $C_{x-y}$ aryl; and (iii) compounds of O and S, oxidation state +2, including ethers, aldehydes, esters, and ketones. In the above class definitions, x is an integer of 1 to 3. A Lewis base, defined as an electron-pair donor, can also act as a Brønsted base since the pair of electrons can be donated to a proton. This means that the Brønsted acid/base concept is not limited to aqueous solutions.

A basic group may also be defined as a species which yields a solution with a hydrogen ion activity lower than that of pure water, i.e. a pH higher than 7.0 at standard conditions. Preferably, the basic group is capable of being protonated by a protic acid.

Accordingly, the basic group may be selected from a primary amine, secondary amine, tertiary amine, anilines, enamine, hydrazine, hydrazone, hydroxylamine, and imine.

Furthermore, when the basic group of $R_3$ contains nitrogen functionality, it may form part of a nitrogen-containing heterocycle. Such a functional group may be selected from azetidine, aziridine, benzothiazole, benzothiazepine, benzothiazine, benzoxazine, benzoxazole, imidazoline, imidazolidine, imidazopyridine, imidazopyrimidine, indole, isoindole, indoline, isoindoline, isothiazole, isoxazole, morpholine, oxazole, oxazoline, oxazolidine, oxathiazole, oxathiazine, piperidine, piperazine, pyrrazoline, pyrrolidine, pyrroline, pyrrolizine, pyridine, pyrrole, tetrazole, triazole, thiazole, thiazoline, thiazine, and thiazolidine.

Preferably, the basic group is selected from a primary amine, secondary amine, tertiary amine, anilines, piperidines, pyridines, indoles, pyrroles, piperazines, aziridines, and morpholines.

In formula (I), X is an anionic species. As such, any anionic species capable of forming a salt with a cationic species may be employed. X may be a carbon anion, a cyanide, an azide, an amine, an alkoxy, a phenolate, a thiolate, a thiophenolate, a cyanate, a thiocyante, a halide (e.g. iodide, bromide, chloride, fluoride), a carboxylate, a carbonate, triflate, mesylate, tosylate, tetrafluoroborate, or hexafluoroantimonate. Preferably, X is selected from halide (e.g. iodide, bromide, chloride, fluoride), triflate, mesylate, tosylate, tetrafluoroborate, and hexafluoroantimonate. A particularly preferred anionic species is triflate.

The value of n in formula (I) is an integer selected from 1 to 5, e.g. 1, 2, 3, 4, or 5. Preferably, n is an integer selected from 1 to 3. Most preferably, n is 1.

In a preferred embodiment, the sulfonium salt has a structure according to formula (I), wherein:

$R_1$ and $R_2$ are the same or different and each is independently selected from an optionally substituted aryl group, an optionally substituted cycloalkyl group, an optionally substituted alkenyl group, and an optionally substituted alkyl group (preferably an optionally substituted aryl group);

W is a bond, an optionally substituted aryl group, an optionally substituted heteroaryl group, or an optionally substituted hyeterocyclyl group (preferably optionally substituted aryl group);

$R_3$ is a moiety comprising at least one basic group selected from amine (including an N-containing-heterocyclyl group);

X is selected from halide (e.g. iodide, bromide, chloride, fluoride), triflate, mesylate, tosylate, tetrafluoroborate, and hexafluoroantimonate; and n is an integer selected from 1 to 3.

In a preferred embodiment, the sulfonium salt has a structure according to formula (I), wherein:

$R_1$ and $R_2$ are the same or different and each is independently selected from a $C_{6-14}$ aryl group, a $C_{2-10}$ alkenyl group, a $C_{1-10}$ alkyl group, and a $C_{3-10}$ cycloalkyl group, each optionally substituted by (1) a group selected from -J-aryl, -J-heteroaryl, -J-heterocyclyl and -J-$C_{3-8}$ cycloalkyl, wherein J represents a bond or $C_{1-6}$ alkylene (preferably methylene), and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl (preferably acetyl), carboxyl, and $C_{1-6}$ alkoxy-carbonyl (preferably methoxycarbonyl);

W is a bond, a $C_{6-14}$ aryl group, or a 5-6 membered monocyclic aromatic or fused 8-10 membered bicyclic aromatic ring in which the monocyclic or bicyclic ring contains 1 to 4 heteroatoms selected from oxygen, nitrogen and sulphur, each optionally substituted by (1) a group selected from -J-aryl, -J-heteroaryl, -J-heterocyclyl and -J-$C_{3-8}$ cycloalkyl, wherein J represents a bond or $C_{1-6}$ alkylene (preferably methylene), and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl (preferably acetyl), carboxyl, and $C_{1-6}$ alkoxy-carbonyl (preferably methoxycarbonyl);

$R_3$ is a moiety comprising at least one basic group selected from an amine (including an N-containing-heterocyclyl group), alcohol, ether, and ketone;

X is selected from triflate, mesylate, tosylate, tetrafluoroborate, and hexafluoroantimonate (preferably triflate); and n is an integer selected from 1 to 3 (preferably n is 1).

In a further preferred embodiment, there is provided a sulfonium salt according to formula (Ia):

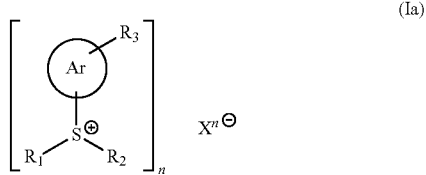

(Ia)

wherein $R_1$ and $R_2$ are the same or different and each is independently selected from an optionally substituted aryl group, an optionally substituted alkenyl group, an optionally substituted alkyl group, an optionally substituted cycloalkyl group, an optionally substituted cycloalkenyl group, an optionally substituted aralkyl group, an optionally substituted arylalkenyl group, an optionally substituted heteroaryl group and an optionally substituted heterocyclyl group, or $R_1$ and $R_2$ are joined together to form an optionally substituted sulfur-containing ring;

Ar is an optionally substituted aryl group or an optionally substituted heteroaryl group;

$R_3$ is a moiety comprising at least one basic group;

X is an anionic species;

and n is an integer selected from 1 to 5.

In a particularly preferred embodiment, the sulfonium salt has a structure according to formula (Ia), wherein:

$R_1$ and $R_2$ are a $C_{6-14}$ aryl group (preferably phenyl) or a $C_{2-10}$ alkenyl group (preferably propenyl or butenyl), each optionally substituted by (1) a group selected from -J-aryl, -J-heteroaryl, -J-heterocyclyl and -J-$C_{3-8}$ cycloalkyl, wherein J represents a bond or $C_{1-6}$ alkylene (preferably methylene), and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl (preferably acetyl), carboxyl, and $C_{1-6}$ alkoxy-carbonyl (preferably methoxycarbonyl);

Ar is a $C_{6-14}$ aryl group (preferably phenyl), or a 5-6 membered monocyclic aromatic or a fused 8-10 membered bicyclic aromatic ring in which the monocyclic or bicyclic ring contains 1 to 4 heteroatoms selected from oxygen, nitrogen and sulphur (preferably pyridyl, indolyl or benzothienyl), each optionally substituted by (1) a group selected from -J-aryl, -J-heteroaryl, -J-heterocyclyl and -J-$C_{3-8}$ cycloalkyl, wherein J represents a bond or $C_{1-6}$ alkylene (preferably methylene), and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl (preferably acetyl), carboxyl, and $C_{1-6}$ alkoxy-carbonyl (preferably methoxycarbonyl);

$R_3$ is a fragment of a known pharmaceutically active agent comprising at least one amine group (including an N-containing-heterocyclyl group);

X is selected from triflate, tetrafluoroborate, and hexafluoroantimonate (preferably triflate); and n is 1.

In another particularly preferred embodiment, the sulfonium salt has a structure according to formula (Ia), wherein:

$R_1$ and $R_2$ are a $C_{6-14}$ aryl group (preferably phenyl), each optionally substituted by one to three substituents selected from $C_{1-6}$ alkyl (preferably methyl, ethyl or isopropyl), and $C_{1-6}$ alkoxy (preferably methoxy), Ar is a $C_{6-14}$ aryl group (preferably phenyl), or a 5-6 membered monocyclic aromatic or a fused 8-10 membered bicyclic aromatic ring in which the monocyclic or bicyclic ring contains 1 to 4 heteroatoms selected from oxygen, nitrogen and sulphur (preferably pyridyl, indolyl or benzothienyl), each optionally substituted by (1) a group selected from -J-aryl, -J-heteroaryl, -J-heterocyclyl and -J-$C_{3-8}$ cycloalkyl, wherein J represents a bond or $C_{1-6}$ alkylene (preferably methylene), and said aryl is selected from phenyl, said heteroaryl is selected from triazolyl, thiazolyl, thienyl, pyrazolyl, pyrimidyl, pyridazinyl, pyrazinyl, and pyridyl, said heterocyclyl is selected from pyrrolidinyl, azetidinyl, pyrazolidinyl, oxazolidinyl, piperidinyl, piperazinyl, morpholinyl, thiomorpholinyl, and thiazolidinyl, and said $C_{3-8}$ cycloalkyl is selected from cyclopropyl, cyclobutyl, cyclopentyl and cyclohexyl; or (2) one to three substituents selected from $C_{1-6}$ alkyl (preferably methyl, ethyl or isopropyl), halogen (preferably Cl or Br), halo$C_{1-6}$ alkyl (preferably trifluoromethyl), cyano, amino, $C_{1-6}$ alkoxy (preferably methoxy), $C_{1-6}$ alkyl-carbonyl (preferably acetyl), carboxyl, and $C_{1-6}$ alkoxy-carbonyl (preferably methoxycarbonyl);

$R_3$ is a fragment of a known pharmaceutically active agent comprising at least one amine group (including an N-containing-heterocyclyl group);

X is selected from triflate, tetrafluoroborate, and hexafluoroantimonate (preferably triflate); and n is 1.

The method of preparing the sulfonium salt according to formula (I) comprises (i) treating a thioether according to formula (II) with an acidic compound so as to form an acid-base adduct by virtue of the basic group of $R_3$, (ii) treating the adduct with a compound according to the formula $[(R_2)_2I]_m^+Z^{m-}$ or formula $[(R_1)(R_2)I]_m^+Z^{m-}$, optionally in the presence of a catalyst, or where $R_1$ and $R_2$ are joined together to form an optionally substituted sulfur-containing ring in formula (I), treating an adduct of formula (II) formed in step (i) in which $R_1$ contains at least one unsaturated bond, with an acid or electrophilic species so as to cause formation of the optionally substituted sulfur-containing ring, and (iii) recovering the product sulfonium salt, wherein $R_1$, $R_2$, W, and $R_3$ are as defined in relation to formula (I) above, Z is a monovalent anionic species, and m is an integer selected from 1 to 5.

Previous methods for preparing sulfonium salts have not been suitable for substrates containing basic groups, such as amines. This is believed to be because the basic group forms a complex with the catalyst used in the reaction, or that the basic group reacts preferentially (e.g. N-arylation) with the thioether, thereby preventing formation of the sulfonium salt. For example, when directly applying the procedure of Crivello et al., *J. Org. Chem.*, 1987, 43, 3055, to diphenyl sulphides bearing amines, no reaction to the desired sulfonium salts took place, most probably because amines complex and reduce copper (II) to copper (I) as well as iodonium salts, thus preventing the reaction.

Accordingly, it was surprisingly found by the present inventors that, in order to keep copper in its oxidation state +2 and therefore make it available as an electron transfer agent, an acid-base adduct could be formed between the amine and an acidic compound, either protic or Lewis acidic, prior to reaction. In this regard, the sulfonium salt is initially treated with an acidic compound so as to form such an adduct, thereby transiently protecting the basic group and preventing it from forming a complex with the catalyst. This method therefore provides the first procedure for preparing sulfonium salts containing basic groups.

Preferably, the acidic compound is a protic acid. In this case, the basic group becomes protonated when treated with the acidic compound. In particular, the acidic compound can be selected from sulfuric acid, fluorosulfuric acid, nitric acid, phosphoric acid, fluoroantimonic acid, fluoroboric acid, hexafluorophosphoric acid, chromic acid, boric acid, methanesulfonic acid, ethanesulfonic acid, benzenesulfonic acid, p-toluenesulfonic acid, trifluoromethanesulfonic acid, trifluoroacetic acid, acetic acid, citric acid, formic acid, hydrogen chloride, hydrogen bromide, and hydrogen iodide. In terms of yield, trifluoromethanesulfonic acid (triflic acid) is most preferred.

The catalyst used in the reaction is preferably a transition metal coordination complex. More preferably, the catalyst is a copper (II) complex.

Where $R_1$ and $R_2$ are joined together to form an optionally substituted sulfur-containing ring in formula (I), and the adduct of formula (II) formed in step (i) in which $R_1$ contains at least one unsaturated bond, is treated with an acid or electrophilic species so as to cause formation of the optionally substituted sulfur-containing ring, an acid (Lewis or Bronsted acid), or an electrophile may be used. Examples of such species include sulfuric acid, fluorosulfuric acid, nitric acid, phosphoric acid, fluoroantimonic acid, fluoroboric acid, hexafluorophosphoric acid, chromic acid, boric acid, methanesulfonic acid, ethanesulfonic acid, benzenesulfonic acid, p-toluenesulfonic acid, trifluoromethanesulfonic acid, trifluoroacetic acid, acetic acid, citric acid, formic acid, hydrogen chloride, hydrogen bromide, hydrogen iodide, NCS, NBS, NIS, or an alkylating agent, such as an alkyl halide, alkyl sulfonate, alkyl triflate, or a carbon cation, or heteroatom cation. Where a Lewis or Bronsted acid is employed, the acid may be the same acid as employed in the formation of the acid-base adduct in step (i).

Sulfonium salts according to the invention may also be prepared by alternative routes involving the oxidative activation of thioethers. For example, by treating a sulfoxide with an acyl chloride (e.g. oxalyl chloride) or anhydride (e.g. triflic anhydride), followed by treating the resulting activated sulfonium salt with a tin or boron species with or without addition of a catalyst (e.g. silver triflate), and recovering the desired sulfonium salt. Suitable sulfoxides include sulfoxide variants of thioethers according to formula (II) (i.e. wherein the S atom is replaced with S=O). Suitable tin or boron species include boronic acid pinacol esters, such as optionally substituted aryl or optionally substituted heteroaryl boronic acid pinacol esters (e.g. 2-aryl- or 2-heteroaryl-4,4,5,5-tetramethyl-1,3,2-dioxaborolane, especially 2-(4-methoxyphenyl)-4,4,5,5-tetramethyl-1,3,2-dioxaborolane).

Z is an anionic species. As such, any anionic species capable of forming a salt with a cationic species may be employed. Preferably, Z is selected from halogen (e.g. iodide, bromide, chloride, fluoride), triflate, mesylate, tosylate, tetrafluoroborate, and hexafluoroantimonate. A particularly preferred anionic species is triflate.

The value of m in formulae $[(R_2)_2I]_m^+Z^{m-}$ and $[(R_1)(R_2)I]_m^+Z^{m-}$ is an integer selected from 1 to 5, e.g. 1, 2, 3, 4, or 5. Preferably, m is an integer selected from 1 to 3. Most preferably, m is 1.

Given that sulfonium salts containing basic groups have not been directly accessed before, previously it has been a significant challenge to efficiently prepare halogenated compounds whereby the halogen is introduced at a late stage of the synthetic route. As such, the present invention also relates to a method of preparing a compound according to formula (III), wherein the method comprises (i) treating a sulfonium salt according to formula (I) with a species capable of generating a nucleophile Y, optionally in the presence of a base and/or chelating agent, and (ii) recovering the compound according to formula (III), wherein $R_3$ are W are as defined in relation to formula (I) above.

The base used in this method is not particularly limited. A preferred base nevertheless is selected from sodium hydroxide, lithium hydroxide, potassium hydroxide, sodium hydrogen carbonate, potassium hydrogen carbonate, sodium carbonate, potassium carbonate, and caesium carbonate. From a practical perspective and in terms of effectiveness, sodium hydrogen carbonate and potassium hydrogen carbonate are especially preferred.

The chelating agent employed may be a cryptand or a crown ether. As such, suitable chelating agents may be selected from 21-cryptand, 211-cryptand, 221-cryptand, 222-cryptand, 222B-cryptand, 12-crown-4, 15-crown-5, 18-crown-6, dibenzo-18-crown-6, and diaza-18-crown-6. Preferably, the chelating agent is a 222-cryptand, such as the commercially available Kryptofix®-222.

Prior art examples of such halogenation reactions teach that heating is required to effect the transformation, as in the case of Mu et al. *Eur. J. Org Chem.* 2012, 5, 889. However, whilst the halogenation procedure of the present invention is also effective at elevated temperatures, it has been surprisingly found that the reaction performs even more smoothly (i.e. fewer by-products formed) under ambient conditions. This is particularly pronounced for substrates in which W in W—$R_3$ is represented by aryl (e.g. phenyl) or heteroaryl (e.g. pyridine), optionally substituted with electron withdrawing groups, and/or wherein $R_3$ is bound to W by way of an electron withdrawing group such as a carbonyl group. For other substrates, heating may be beneficial. Therefore, it is preferable that this method is carried out at room pressure and at a temperature of less than 60° C., for example at less than 55° C., less than 50° C., or less than 45° C. Most preferably, the reaction is performed at room temperature.

The species capable of generating a nucleophile Y may be selected from a hydrocarbon species capable of forming a carbon anion, an amine, an amide, an alkoxy group, a phenolate, a thiolate, a thiophenolate, a cyanate, a thiocyanate, and a halide (preferably halide), including radioactive variants thereof (e.g. fluoride-18). Preferably, the species capable of generating a nucleophile Y may be selected from a hydrocarbon species capable of forming a carbon anion, and a halide (preferably fluoride), including radioactive variants thereof (e.g. fluoride-18). In this context, a nucleophile is a species that donates an electron-pair to an electrophile to form a covalent bond. Thus, any molecules or ions with a free pair of electrons or at least one pi bond can act as a nucleophile.

In particular, the nucleophile may be a compound according to the formula H—Y, where Y is a halide. Preferably, Y is fluoride (or fluoride-18).

In a certain embodiment of the invention, a compound according to formula (III) may be prepared by the method comprising:
i) treating a thioether according to formula (II)

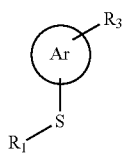

(II)

with an acidic compound so as to form an acid-base adduct by virtue of the basic group of $R_3$;
ii) treating the adduct with a compound according to the formula $[(R_2)_2I]_m^+Z^{m-}$ or formula $[(R_1)(R_2)I]_m^+Z^{m-}$, optionally in the presence of a catalyst, or where $R_1$ and $R_2$ are joined together to form an optionally substituted sulfur-containing ring in formula (I), treating an adduct of formula (II) formed in step (i) in which $R_1$ contains at least one unsaturated bond, with an acid or electrophilic species so as to cause formation of the optionally substituted sulfur-containing ring; and
iii) recovering a sulfonium salt according to formula (I), followed by
iv) treating the sulfonium salt according to formula (I) with a species capable of generating a nucleophile Y, optionally in the presence of a base and/or a chelating agent; and
v) recovering the compound according to formula (III), wherein $R_1$, $R_2$, $R_3$ and Ar are as defined in relation to the sulfonium salt of formula (I), Z is an anionic species, and m is an integer selected from 1 to 5.

It has also been found that the sulfonium salts of the present invention may be used to trap fluoride-18 on solid phase extraction (SPE) cartridges. The positive charge of the sulfonium salts can be used to trap fluoride-18 from, for example, cyclotron target water on disposable solid phase extraction (SPE) cartridges, which thus allows for on-line concentration and solid phase reactions. In particular, this protocol is especially effective using reversed phase cartridges (e.g. Sep-Pak® light and plus (Waters), and Strata® (Phenomenex)) with minimal loss of fluoride-18 under a variety of conditions. In order to confirm that the sulfonium cation, but not the amine in the precursor, is responsible for trapping of fluoride, an experiment using the unsubstituted triphenylsulfoniumtriflate was successfully performed.

The present invention therefore also relates to a solid phase adsorbent comprising a sulfonium salt according to formula (I). The sulfonium salts may be linked to the solid phase adsorbent by chemical or physical means. Thus, the salts may be linked by one or more covalent bonds, or may be adsorbed to the surface of the adsorbent by physical forces, such as van der Waals forces or ionic interactions. In particular, the solid phase adsorbent may be presented in conjunction with a column or cartridge.

In terms of practicality, the solid phase adsorbent is preferably a reversed phase or ion exchange adsorbent. The solid phase adsorbent may be provided as a powder or in the form of a cartridge. Preferably, the solid phase adsorbent is presented in conjunction with a cartridge. The cartridge may take the form of a column having a substantially inert casing into which the adsorbent is loaded, and an inlet and outlet for the passage solution phase reactants, products and by-products. The cartridge containing the sulfonium salt may be manufactured under GMP conditions in order to facilitate clinical production of biologically active compounds and radiopharmaceuticals.

When the sulfonium salts are preloaded onto SPE cartridges, the desired halogented (e.g. $^{18}F$ radionuclide-labelled) compounds may be produced with improved efficiency and purity, thereby enabling swift production at the location the compound is to be administered to the patient. The cartridges also allow for easy replacement and/or recycling.

The invention will now be described in more detail by way of example only, and with reference to the following figures.

BRIEF DESCRIPTION OF THE FIGURES

Figures containing multiple results have been ordered in accordance with the ordering presented in the respective legend.

EXAMPLES

Figure 1:
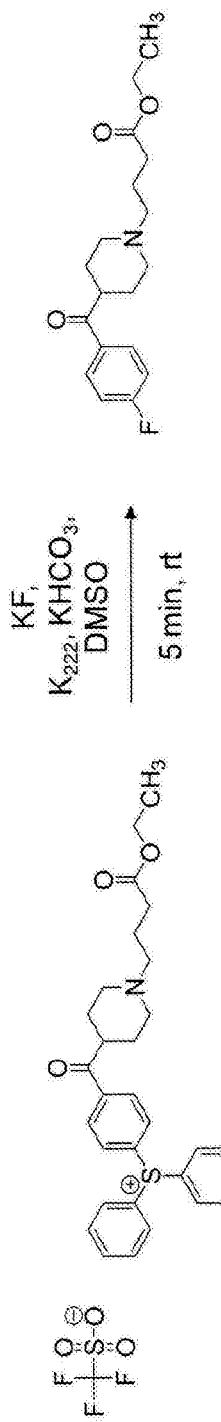
FIG. 1. Analytical results of the reaction of precursor P4 to fluorinated compound 4. HPLC UV detection (254 nm) showed that after 5 minutes precursor P4 (expected retention time ~10 min) had been consumed almost quantitatively and the two expected products, the desired fluorinated compound 4 as well as the by-product diphenyl sulphide, had been formed.
Figure 1:
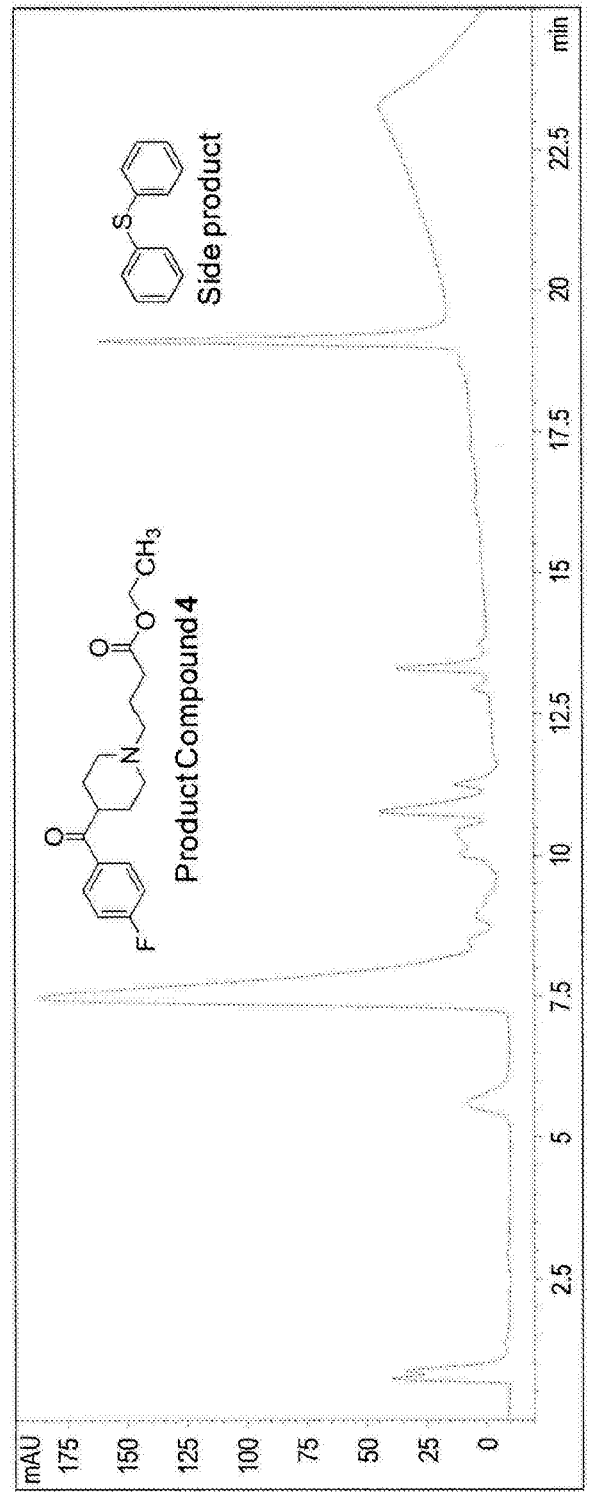

Example 1—General Procedure for the Preparation of Sulfonium Salts

The respective diphenyl sulphide was dissolved in chlorobenzene (1.0 ml/100 mg) and treated with trifluoromethanesulfonic acid (1 equivalent per amine). Under inert atmosphere, diphenyliodoniumtriflate (1 equivalent) and copper (II) benzoate (0.05 equivalents) were added and the mixture was heated at 125° C. for 1 h. During this time, a brown oil separated from the colourless solution. After cooling, diethyl ether was repeatedly added (3×10 ml) to the brown oil and subsequently decanted to remove chloro- and iodobenzenes. The crude mixture was purified by flash column chromatography on silica. The resulting oil was taken up in methylene chloride and washed with sodium hydroxide solution (2 N) and a saturated solution of sodium triflate. The organic layer was dried over magnesium sulphate, filtered and concentrated under reduced pressure to give the desired precursor as oil. Compounds were characterised by NMR and high resolution mass spectrometry.

Example 2—Preparation and Characterisation of Compound P3 ((4-(1-(4-Acetoxybutyl)piperidine-4-carbonyl)phenyl)diphenylsulfonium trifluoromethanesulfonate)

Under inert atmosphere, 4-(4-(4-(phenylthio)benzoyl)piperidin-1-yl)butyl acetate (100 mg, 0.24 mmol) was dissolved in chlorobenzene (1 ml). Trifluoromethanesulfonic acid (0.02 ml, 0.24 mmol), diphenyliodonium triflate (100 mg, 0.24 mmol) and copper(II) benzoate (4 mg, 0.012 mmol) were added and the mixture was heated at 125° C. for 1 h. After cooling, diethyl ether (3×10 ml) was repeatedly added to the brown oil and subsequently decanted to remove chloro- and iodobenzenes. The brown oil was purified by column chromatography (methylene chloride:methanol=10: 0→9:1). The resulting oil was taken up in methylene chloride and washed with sodium hydroxide solution (2 N) and a saturated solution of sodium triflate. The organic layer was dried over magnesium sulphate, filtered and concentrated under reduced pressure to give a colourless oil (90 mg, 60%).

$^1$H NMR (DMSO-d$_6$, 600 MHz) δ(ppm): 8.26 (d, 2H, J=8.64 Hz, ph-2,6H), 7.92 (d, 2H, J=8.64 Hz, ph-3,5H), 7.93-7.86 (m, 6H, ph'-2,4,6H), 7.80 (t, 4H, J=7.86 Hz, ph'-3,5H), 4.00 (t, 2H, J=6.48 Hz, but-4H$_2$), 3.46 (br s, 1H, pip-4H), 2.98 (br s, 2H, pip-2,6H$^{eq}$), 2.43 (br s, 2H, but-1H$_2$), 2.20 (br s, 2H, pip-2,6H$^{ax}$), 2.00 (s, 3H, COCH$_3$), 1.81 (d, 2H, J=12.24 Hz, pip-3,5H$^{eq}$), 1.60-1.50 (m, 6H, but-2, 3H$_2$), $^{13}$C NMR (DMSO-d$_6$, 150 MHz) δ: 201.67 (C=O$^{ketone}$), 170.47 (C=O$^{acetyl}$), 139.56 (ph-4C), 134.60 (ph-3,5C), 131.62 (ph'-2-6C), 130.48 (ph-2,6C), 129.88 (ph-1C), 124.88 (ph'-1C), 120.69 (q, $^1J_{C,F}$=320.55 Hz, CF$_3$), 63.67 (but-4C), 57.10 (but-1C), 52.14 (pip-2,6C), 42.84 (pip-4C), 27.68 (but-3C), 26.02 (pip-3,5C), 22.33 (but-2C), 20.78 (COCH$_3$). $^{19}$F NMR (DMSO-d$_6$, 282 MHz): −78.20 (CF$_3$). TOF MS ES+: 488.2274 (100%, calc 488.2259).

Example 3—Sulfonium Salt Precursors

Each sulfonium salt was isolated as a triflate salt.

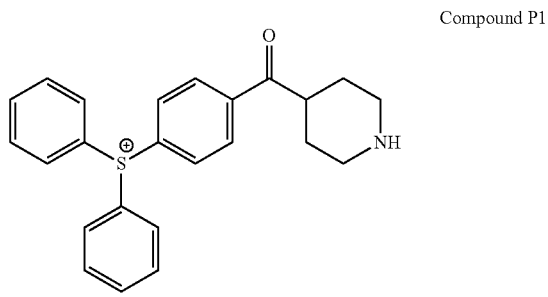

Compound P1

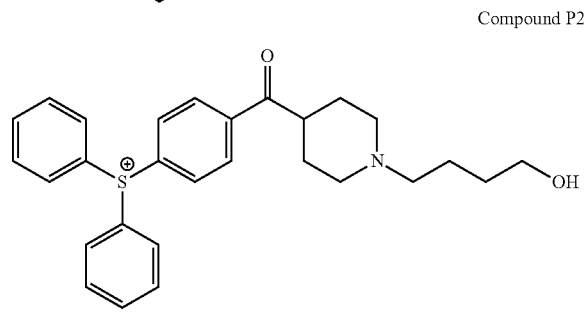

Compound P2

Compound P3
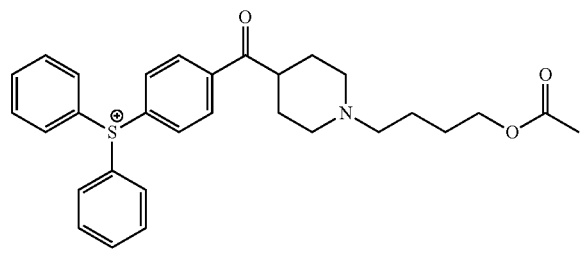
Compound P4
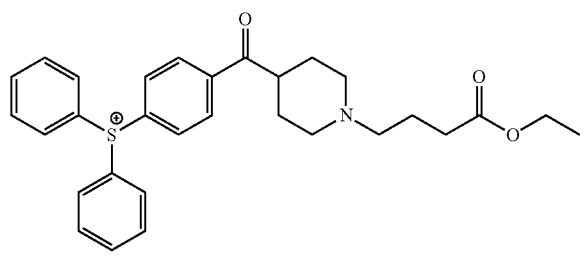
Compound P5
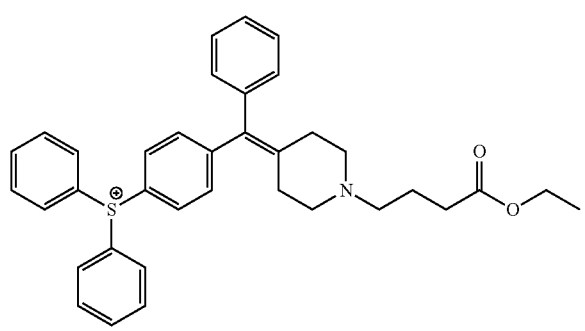
Compound P6
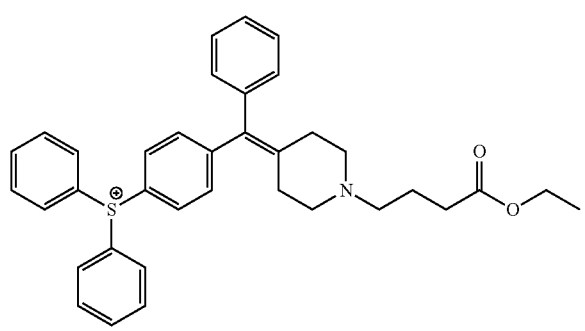
Compound P7
Compound P8
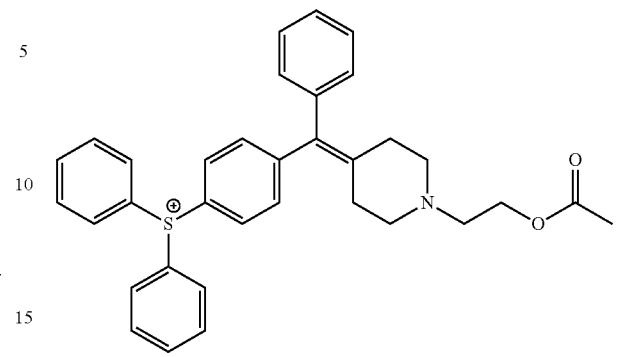
Compound P9
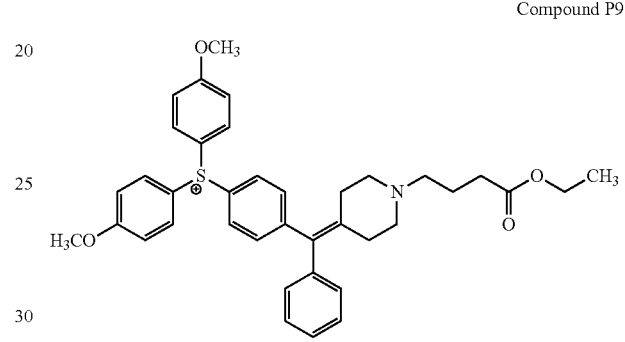
Compound P10
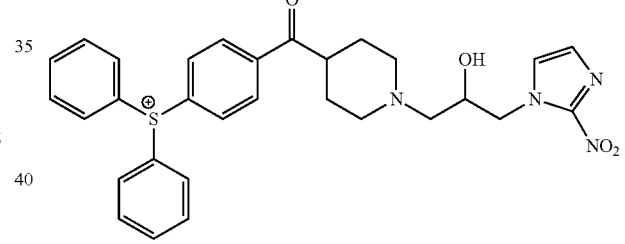
Compound P11
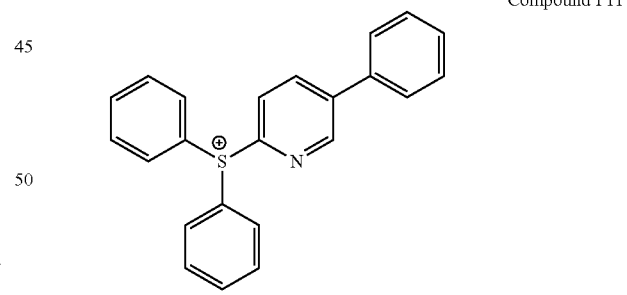
Compound P12
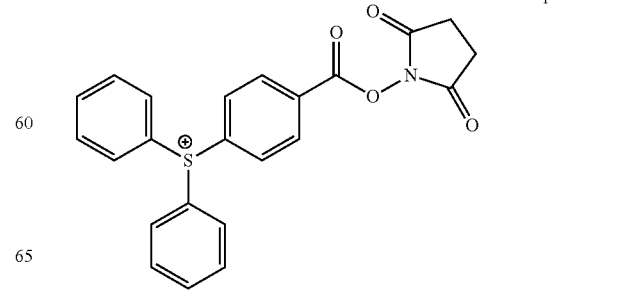

Compound P13

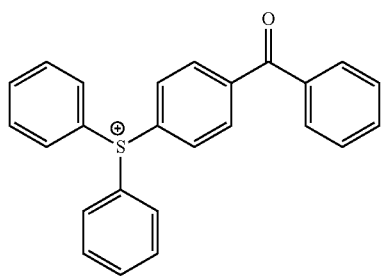

Compound P14

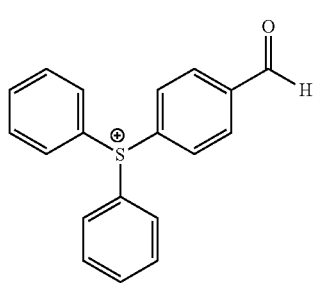

Compound P15

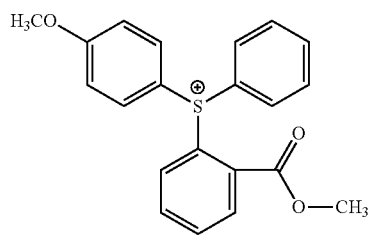

Compound P16 (Reference)

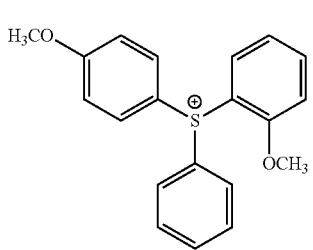

Compound P17 (Reference)

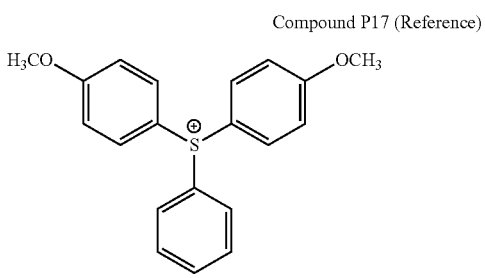

Compound P18 (Reference)

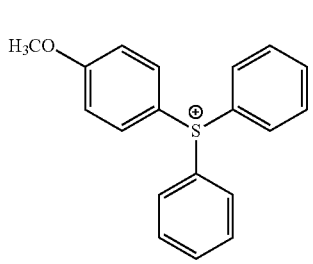

Compound P19 (Reference)

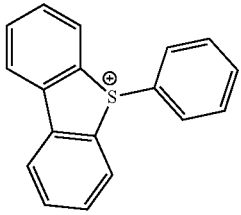

Compound P20 (Reference)

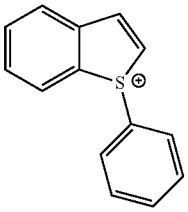

Example 4—Preparation of Sulfonium Salt Precursors Bearing Aliphatic Moieties

A thioether bearing an alkenyl residue in the ortho position (with $R^1$ and $R^2$ being alkyl or aryl groups) can be treated with an electrophile (e.g. $Br_2$ or ICl) to cyclise to a benzothiophenium ion. If residue $R_3$ is, for example, an aliphatic structure that also exhibits a basic moiety, sulfonium salts for the functionalisation of aliphatic residues can be prepared.

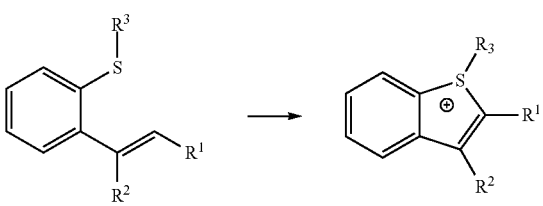

Example 5—General Method for Functionalisation of Sulfonium Salts

Under inert conditions, the respective sulfonium salt precursor was added to a species capable of generating a nucleophile Y (as defined above) with or without addition of a base and/or chelator in a suitable solvent (or solvent mixture). The mixture was stirred for times between 1 and 15 minutes at temperatures up to 150° C., usually up to 60° C. Work-up, purification and isolation were performed according to the physicochemical properties of the reactants used and according to the scale of the reaction (preparative/analytical).

Example 6—Preparation of ethyl 4-(4-(4-fluorobenzoyl)piperidin-1-yl)butanoate (4) from (4-(1-(4-ethoxy-4-oxobutyl)piperidine-4-carbonyl)phenyl)diphenylsulfonium trifluoromethanesulfonate (P4) on an Analytical Scale To a solution of potassium fluoride (0.09 mg) in water (28 μl) was added a solution of Kryptofix®-222 and potassium bicarbonate (30 mM each) in acetonitrile (0.5 ml) containing 15% water. The resulting solution was azeotropically dried at 100° C. and under a stream of nitrogen. Acetonitrile (0.5 ml) was added, and the distillation was continued, this procedure being repeated. The reaction vial was subsequently closed and, after cooling to ambient temperature, (4-(1-(4-ethoxy-4-oxobutyl)piperidine-4-carbonyl)phenyl) diphenylsulfonium trifluoromethanesulfonate (P4; 1 mg, 1 equivalent related to fluoride) dissolved in dimethyl sulfoxide (0.5 ml) was added. The mixture was stirred for 5 minutes at room temperature. It was subsequently quenched with water (4.5 ml) and analysed by HPLC using a Chromolith Performance RP18-e column (100×4.6 mm) at room temperature. The mobile phase consisted of water and methanol (each containing 0.5% TFA). Elution started with an isocratic solvent mixture containing 10% methanol that, after 5 minutes was increased to 90% in 17 minutes (FIG. 1).

Example 7—General Fluorination Procedure Using $^{18}$F

Fluoride-18 in water (50-150 MBq) was trapped on a Sep-Pak® Accell Plus QMA Plus Light Cartridge (Waters) and released with a solution of Kryptofix®-222 and potassium bicarbonate (30 mM each) in acetonitrile (0.5 ml) containing 15% water. The resulting solution was azeotropically dried at 100° C. and under a stream of nitrogen. Acetonitrile (0.5 ml) was added, and the distillation was continued, this procedure being repeated. The reaction vial was subsequently closed and, after cooling to ambient temperature, the sulfonium precursor dissolved in dimethyl sulfoxide (0.5 ml) was added. The mixture was stirred for 15 minutes at 110° C. After cooling, it was quenched with water (1.5 ml) and purified by HPLC using a Chromolith SemiPrep RP18-e column (100×10 mm) at room temperature. The mobile phase consisted of water and methanol (each containing 0.5% TFA). Gradient elution starting with 10% methanol content that was increased to 90% allowed for isolation of the respective radioactive product (method slightly modified for each product). The identity of the radiolabelled product was confirmed by HPLC co-injection of the non-radiolabelled analogue.

Example 8—Preparation and Characterisation of [$^{18}$F](4-Fluorophenyl)(piperidin-4-yl)methanone ([$^{18}$F]1)

Figure 2:
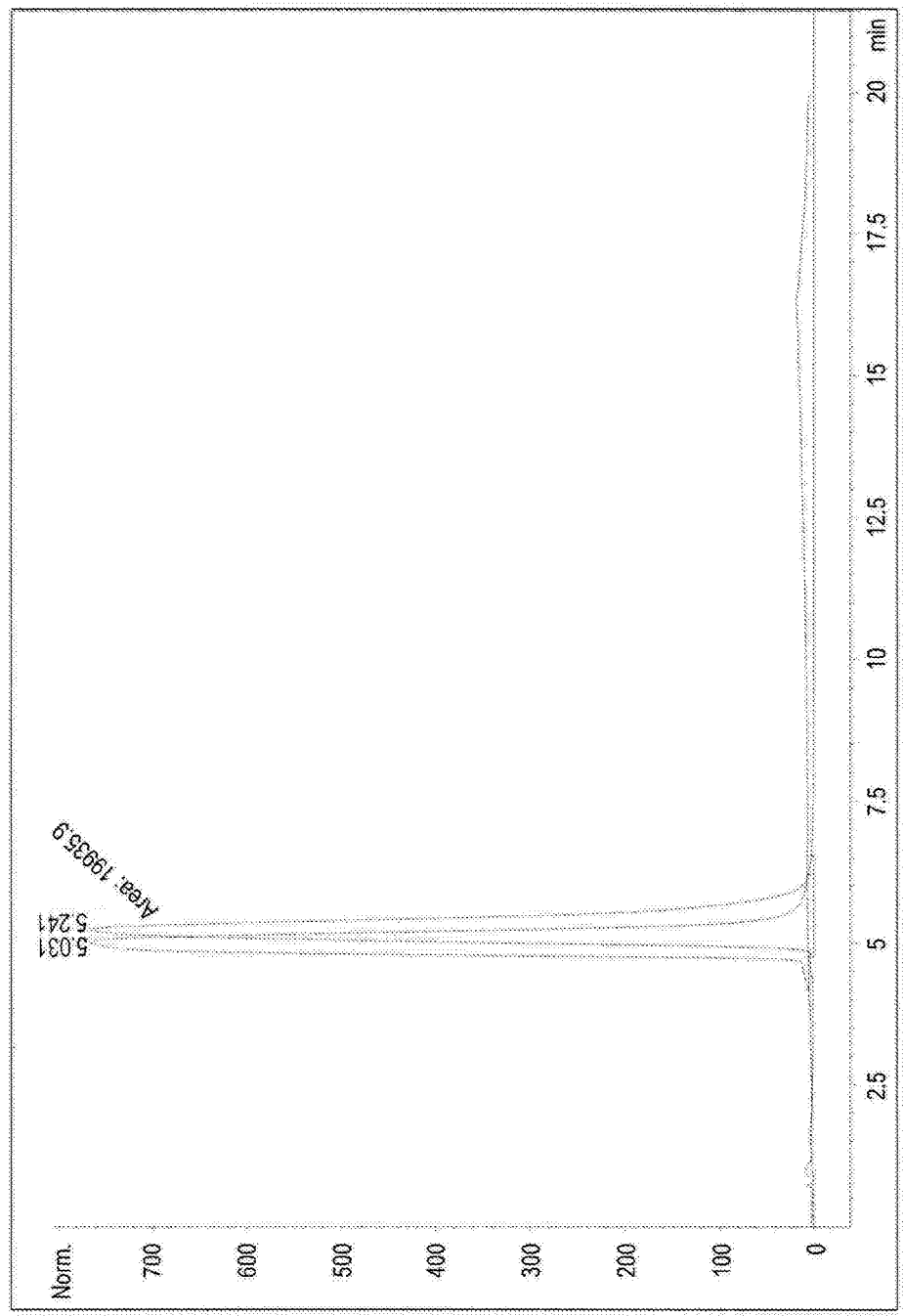
FIG. 2. Identification of the radiolabelled product of the reaction of Example 8. HPLC chromatogram showing UV (254 nm; left peak) and radioactivity (right peak) detection.

Fluoride-18 in water (115.0 MBq) was trapped on a Sep-Pak® AccellPlus QMA Plus Light Cartridge (Waters) and released with a solution of Kryptofix®-222 and potassium bicarbonate (30 mM each) in acetonitrile (0.5 ml) containing 15% water. The resulting solution was azeotropically dried at 100° C. and under a stream of nitrogen. Acetonitrile (0.5 ml) was added, and the distillation was continued, this procedure being repeated. The reaction vial was subsequently closed and, after cooling to ambient temperature, diphenyl(4-(piperidine-4-carbonyl)phenyl)sulfonium trifluoromethanesulfonate (P1) dissolved in dimethyl sulfoxide (0.5 ml) was added. The mixture was stirred for 15 minutes at 110° C. After cooling, it was quenched with water (1.5 ml) and purified by HPLC using a Chromolith SemiPrep RP18-e column (100×10 mm) at room temperature. The mobile phase consisted of water and methanol (each containing 0.5% TFA). At a flow rate of 5 ml/minute, isocratic elution (10% methanol content for 5 minutes) was followed by gradient elution starting with 10% methanol that was increased to 90% in 15 minutes. [$^{18}$F](4-Fluorophenyl)(piperidin-4-yl)methanone ([$^{18}$F]1) was isolated. In this specific example, the analytical radiochemical yield (RCY) was 31%, and the decay-corrected isolated RCY was 21%. The identity of the radiolabelled product was confirmed by HPLC co-injection of the non-radiolabelled analogue (compound 1) using a Chromolith Performance RP18-e column (100×4.6 mm) at room temperature. The mobile phase consisted of water and methanol (each containing 0.5% TFA). At a flow rate of 3 ml/minute, the organic content was increased from 1% to 40% in 15 minutes. Compounds showed a retention time of ~5.1 minutes (FIG. 2). The radiochemical purity of the isolated labelled product was 99%.

Example 9—Compounds Functionalised with Fluorine-18

| Precursor (each isolated as a triflate salt) | Product (standard reagents and conditions unless specified otherwise: [$^{18}$F]F$^-$, K$_{222}$, KHCO$_3$, DMSO, 15 min) | Analytical RCY [%] | Isolated RCY [%] |
|---|---|---|---|
| 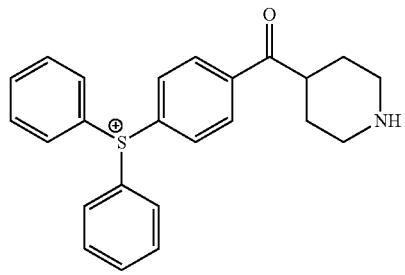 [SMILES: O=C(c1ccc([S+](c2ccccc2)c2ccccc2)cc1)C1CCNCC1]<br>Compound P1 | 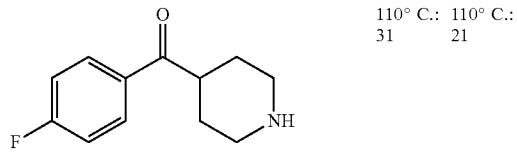<br>Compound [$^{18}$F]1 | 110° C.:<br>31 | 110° C.:<br>21 |

| Precursor (each isolated as a triflate salt) | Product (standard reagents and conditions unless specified otherwise: [$^{18}$F]F$^-$, K$_{222}$, KHCO$_3$, DMSO, 15 min) | Analytical RCY [%] | Isolated RCY [%] |
|---|---|---|---|
| Compound P2 | Compound [$^{18}$F]2 | 110° C.: 33 | 110° C.: 21 |
| Compound P3 | Compound [$^{18}$F]3 | 110° C.: 61 <br> 50° C.: 36 | 110° C.: 39 <br> 50° C.: 19 |
| Compound P5 | Compound [$^{18}$F]5 | 110° C.: 21 | 110° C.: 10 |
| Compound P6 | Compound [$^{18}$F]6 | 110° C.: <10 | n.d. |

-continued

| Precursor (each isolated as a triflate salt) | Product (standard reagents and conditions unless specified otherwise: [$^{18}$F]F$^-$, K$_{222}$, KHCO$_3$, DMSO, 15 min) | Analytical RCY [%] | Isolated RCY [%] |
|---|---|---|---|
| Compound P9 | Compound [$^{18}$F]5 | 110° C.: 31 | 110° C.: 15 |
| Compound P10 | Compound [$^{18}$F]10 | 110° C.: <10 | n.d. |
| Compound P11 | Compound [$^{18}$F]11 | 110° C.: 84<br>50° C.: 80<br>25° C.: 68 | 110° C.: 54<br>50°C.: 51<br>25° C.: 41 |
| Compound P13 | Compound [$^{18}$F]13 | 110° C.: 68<br>50° C.: 61<br>25° C.: 31 | 110° C.: 54<br>50° C.: 40<br>25° C.: 22 |

-continued

| Precursor (each isolated as a triflate salt) | Product (standard reagents and conditions unless specified otherwise: [$^{18}$F]F$^-$, K$_{222}$, KHCO$_3$, DMSO, 15 min) | Analytical RCY [%] | Isolated RCY [%] |
|---|---|---|---|
| 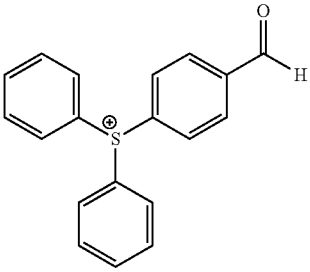 [SMILES: O=Cc1ccc([S+](c2ccccc2)c2ccccc2)cc1]<br>Compound P14 | 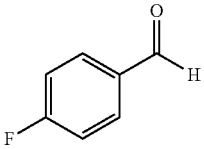<br>Compound [$^{18}$F]14 | 50° C.:<br>37 | 50° C.:<br>24 |
| 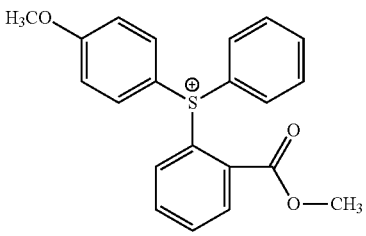 [SMILES: COC(=O)c1ccccc1[S+](c1ccccc1)c1ccc(OC)cc1]<br>Compound P15 | 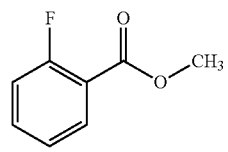<br>Compound [$^{18}$F]15 | 110° C.:<br>73<br>50° C.:<br>34<br>n = 1 | n.d. |
| 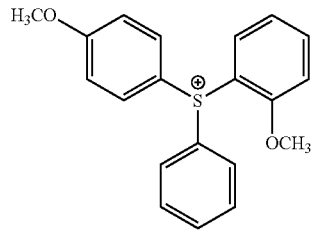<br>Compound P16 | 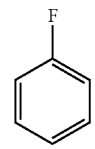<br>Compound [$^{18}$F]16 | 150° C., 15 min:<br>40 | 150° C., 15 min:<br>17 |
| 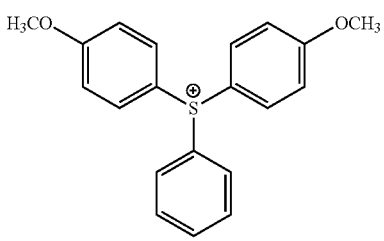 [SMILES: COc1ccc([S+](c2ccccc2)c2ccc(OC)cc2)cc1]<br>Compound P17 | 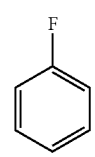<br>Compound [$^{18}$F]16 | 150° C.:<br>40 | 150° C.:<br>13 |
| 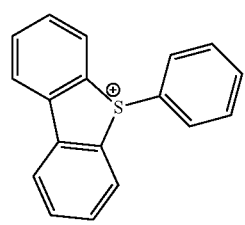 [SMILES: c1ccc(-[s+]2c3ccccc3c3ccccc32)cc1]<br>Compound P18 | 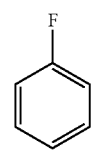<br>Compound [$^{18}$F]16 | 110° C.:<br>53 | 110° C.:<br>16 |

Figure 3:
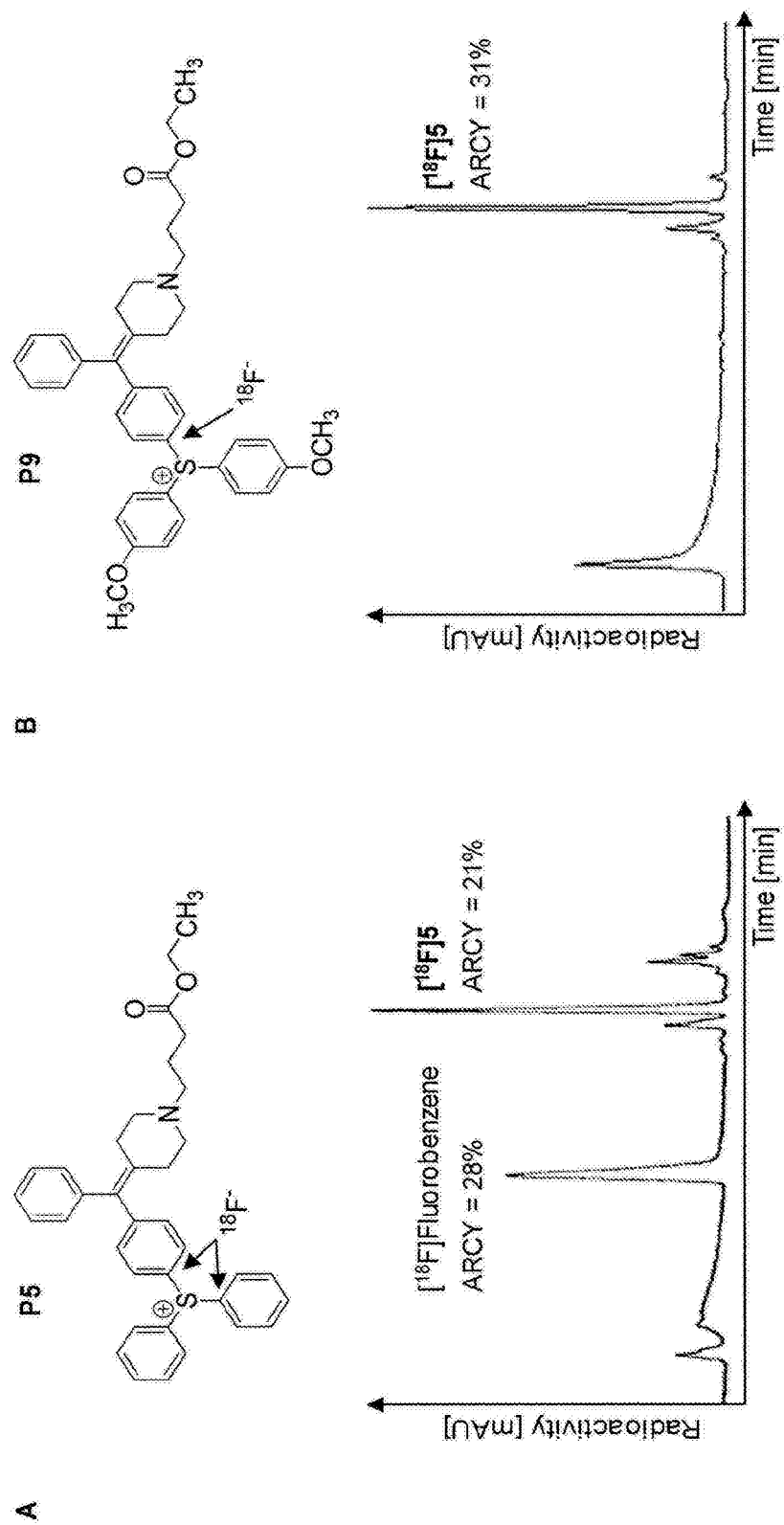
FIG. 3. Analytical results (HPLC chromatograms showing radioactivity detection) of the reaction of precursors P5 and P9 to fluorinated compound [$^{18}F$]5.

These results show that sulfonium salts bearing amines, alcohols and esters functionalities were successfully labelled with fluoride-18 in moderate to good yields. Activation of the para-substituted aryl ring (compounds [$^{18}$F]1-[$^{18}$F]3) generally led to higher yields as compared to those compounds that were not activated (compound [$^{18}$F]5). However, alkene compound [$^{18}$F]5 could be labelled in 10% isolated radiochemical yield (RCY), which is enough to allow tracer preparation for imaging. Interestingly, compounds exhibiting hydrogen bond donors like the secondary amine in compound [$^{18}$F]1 or the primary alcohol in compound [$^{18}$F]2 could also be labelled without protecting groups. In addition, a comparison of sulfonium salts P5 and P9 showed that salts containing deactivated aryl substituents, i.e. the anisole groups in P9, exhibited excellent regioselectivity, with no detected formation of [$^{18}$F]4-fluoroanisole products (FIG. 3). A corresponding result was obtained for P14 and P15. On the other hand, a small amount of [$^{18}$F]4-fluorobenzene was isolated in the case of P5. Conformational restraints in P17 also led to good regioselectivity. Each experiment was performed in triplicate (unless stated otherwise, i.e. n=1 means that the experiment was performed once) and the radiochemical yield (RCY) determined as an average. Transformations P16-P18 to [$^{18}$F]16 are for reference only.

Example 10—Fluorination at Room Temperature

Triarylsulfonium salts can undergo photolytic cleavage after irradiation with short UV light following a heterolytic pathway. In order to evaluate this mechanism as a potential fluorination/labelling method, the reaction of precursor compound P4 to tracer compound [$^{18}$F]4 was further investigated. Reactions at room temperature with and without UV irradiation (254 nm) were performed and compared to that performed as described above.

| Reaction | Conditions | Analytical RCY [%] |
| --- | --- | --- |
| 1 | 110° C., electric lighting | 47.7 |
| 2 | Room temperature, electric lighting | 18.8 |
| 3 | Room temperature, UV (254 nm) | 11.6 |
| 4 | Room temperature, under light exclusion | 17.5 |

Figure 4:
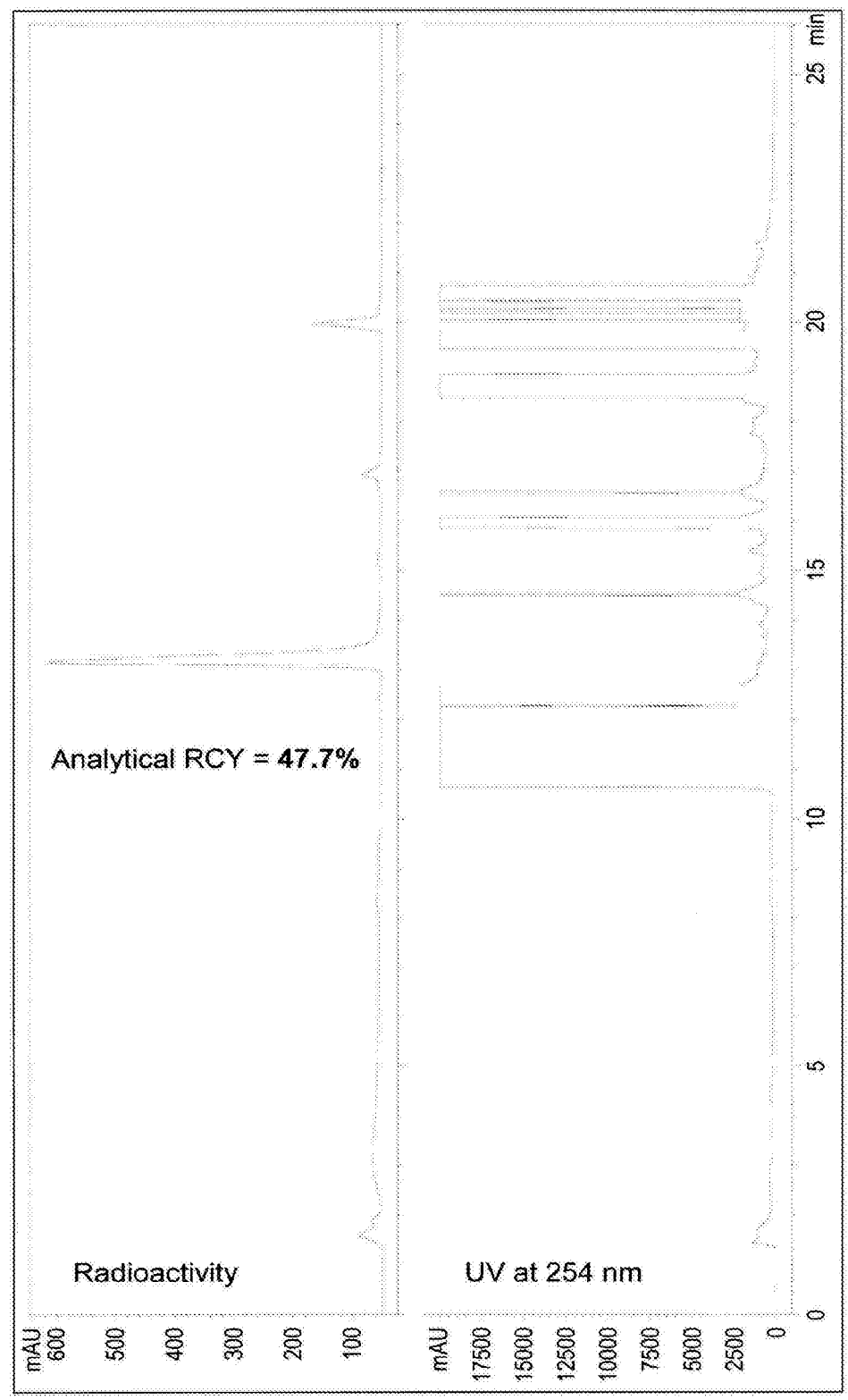
FIG. 4. Analytical results of reaction 1 of Example 10. HPLC chromatogram (top panel: radioactivity detection; bottom panel: UV detection at 254 nm) of the quenched crude reaction mixture after heating (110° C.) indicating formation of the desired radiolabelled product in very good yield but also revealing side product formation and decomposition of precursors.
Figure 5:
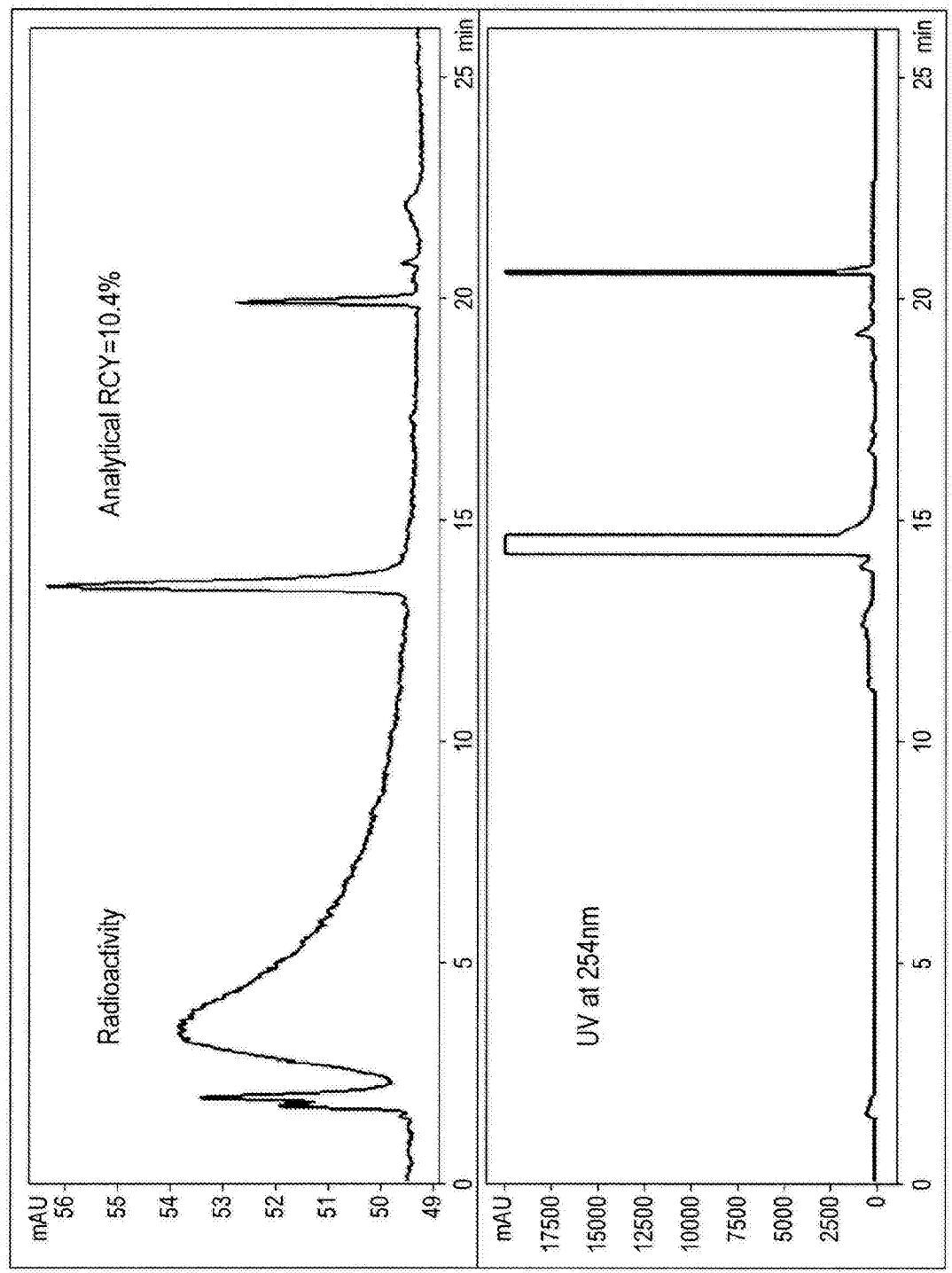
FIG. 5. Analytical results of reaction 3 of Example 10. HPLC chromatogram (top panel: radioactivity detection; bottom panel: UV detection at 254 nm) of the quenched crude reaction mixture after UV irradiation (254 nm) indicating formation of the desired radiolabelled product in moderate yield but also revealing light-induced decomposition of precursors.
Figure 6:
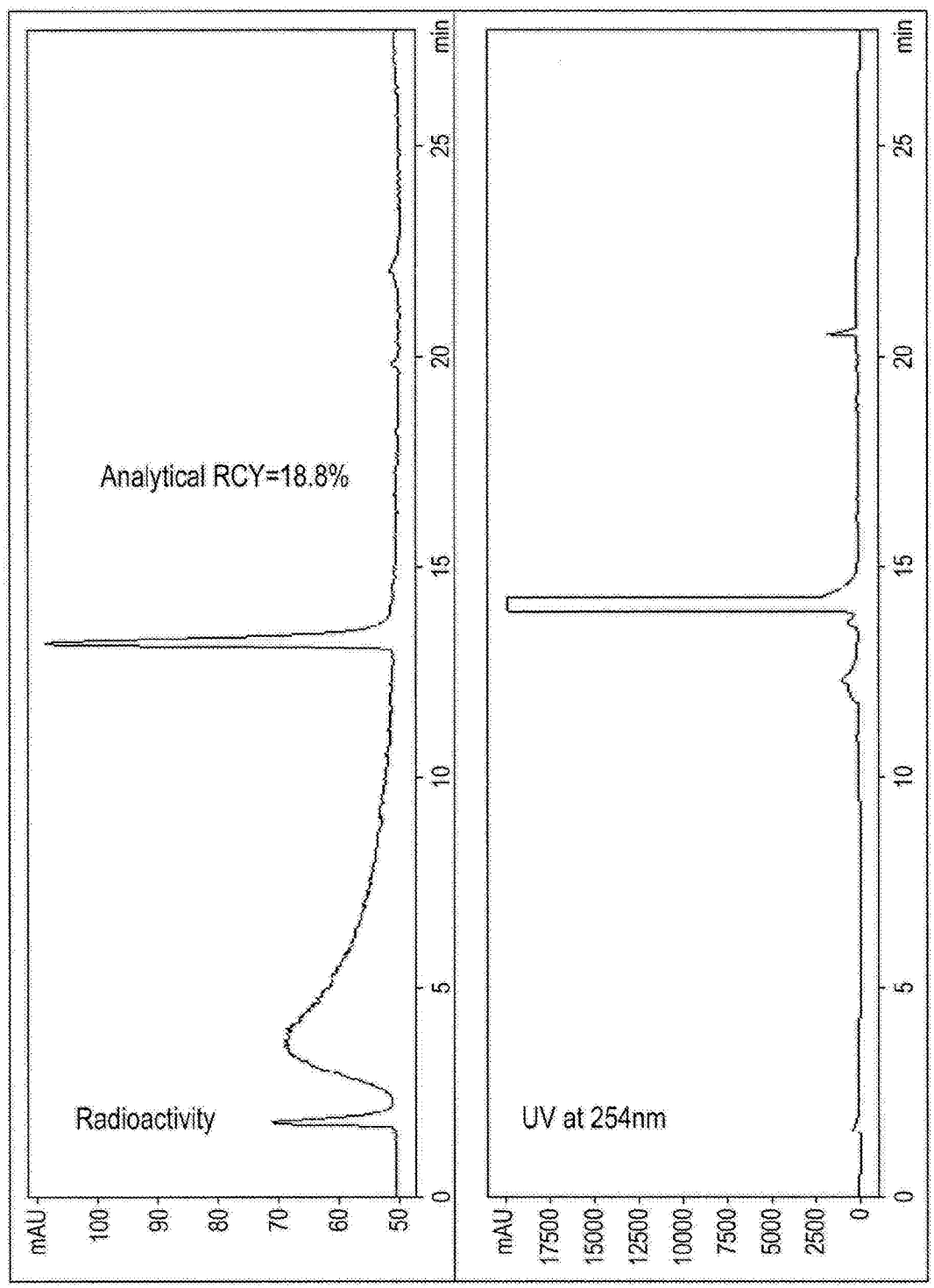
FIG. 6. Analytical results of reaction 4 of Example 10. HPLC chromatogram (top panel: radioactivity detection; bottom panel: UV detection at 254 nm) of the quenched crude reaction mixture after stirring at room temperature indicating formation of the desired radiolabelled product in good yield and without formation of side products/decomposition of precursors.
Figure 7:
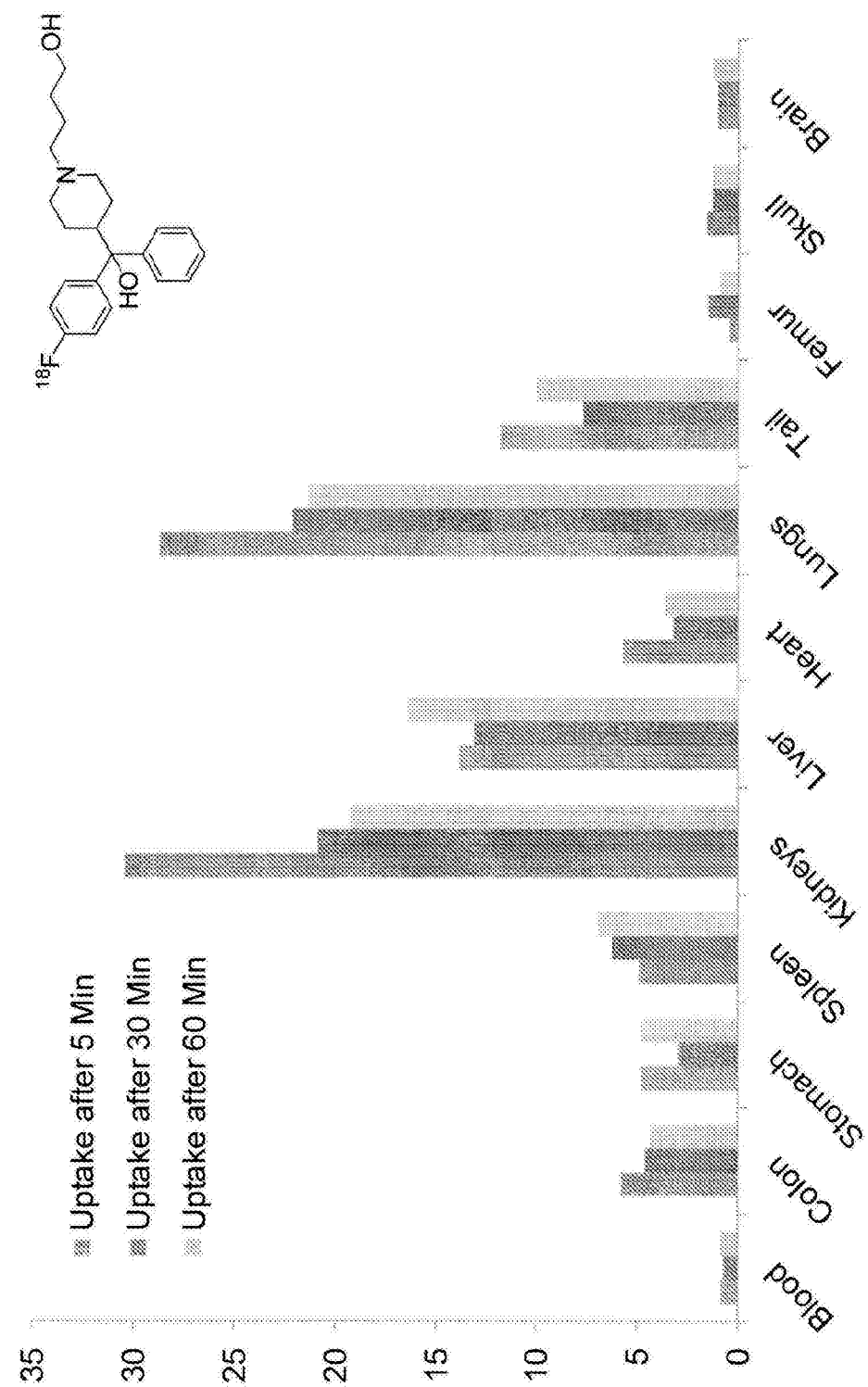
FIG. 7. Biodistribution results 5, 30 and 60 minutes after administration of an $^{18}$F-labelled prodrug. The synthesis of the compound involved labelling of sulfonium salt P3, followed by reaction of the obtained radiolabelled intermediate [$^{18}$F]3 with phenylmagnesium bromide in a Grignard reaction.
Figure 8:
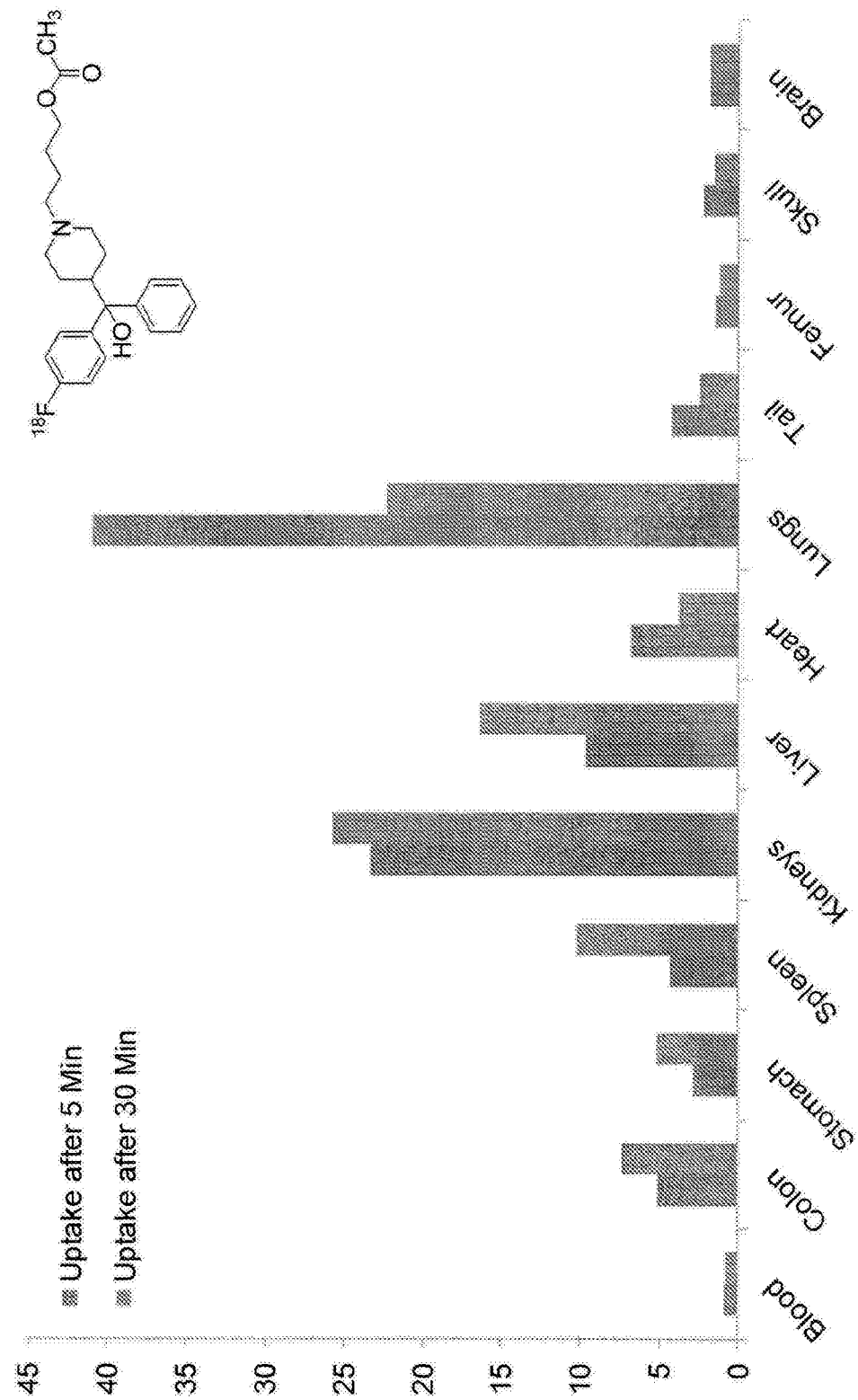
FIG. 8. Biodistribution results 5 and 30 minutes after administration of an $^{18}$F-labelled prodrug. The synthesis of the compound involved labelling of sulfonium salt P3, followed by reaction of the obtained radiolabelled intermediate [$^{18}$F]3 with phenylmagnesium bromide in a Grignard reaction and subsequent acylation of the alcohol with acetyl chloride.
Figure 9:
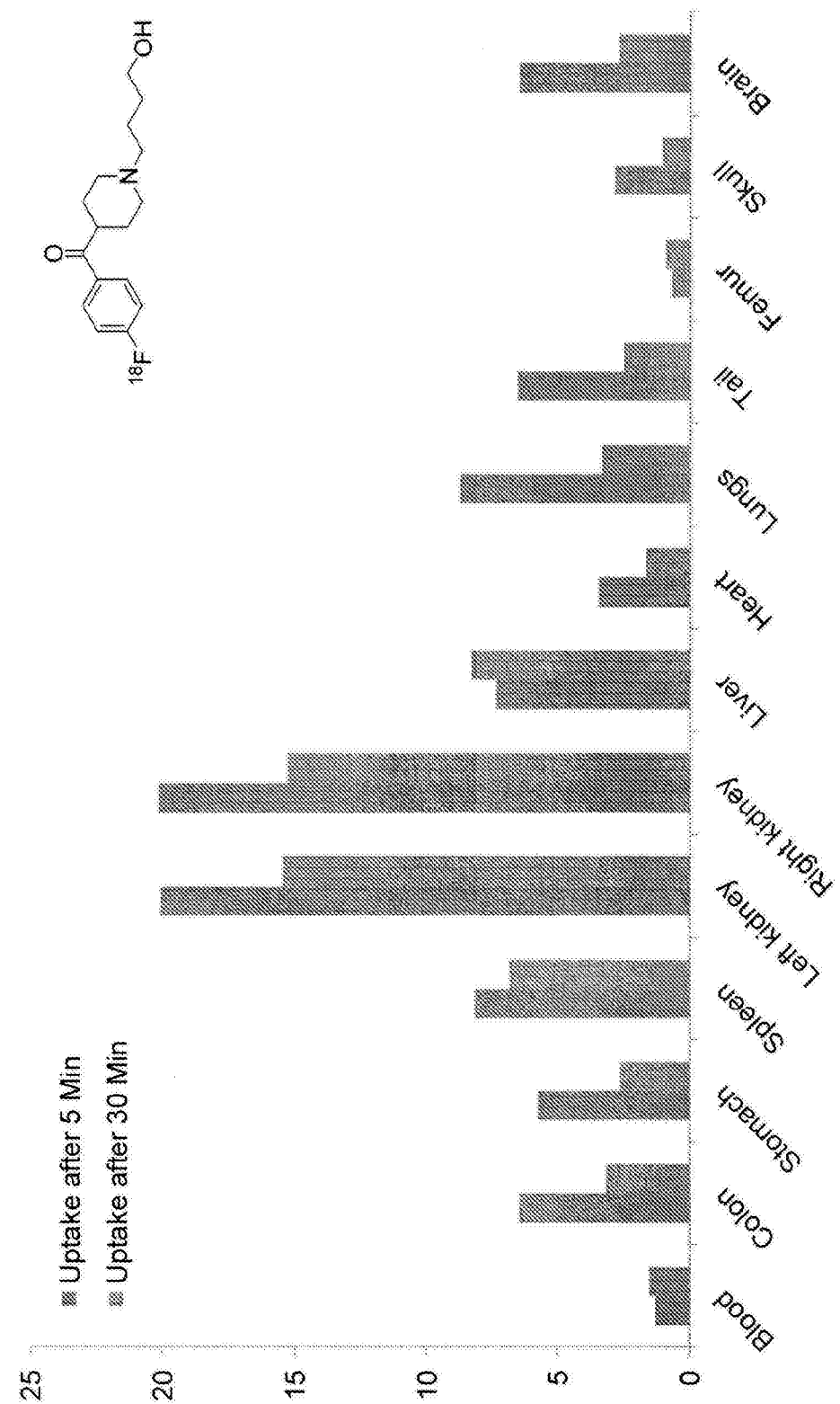
FIG. 9. Biodistribution results 5 and 30 minutes after administration of compound [$^{18}$F]2 after direct labelling of sulfonium salt P2 with fluoride-18.
Figure 10:
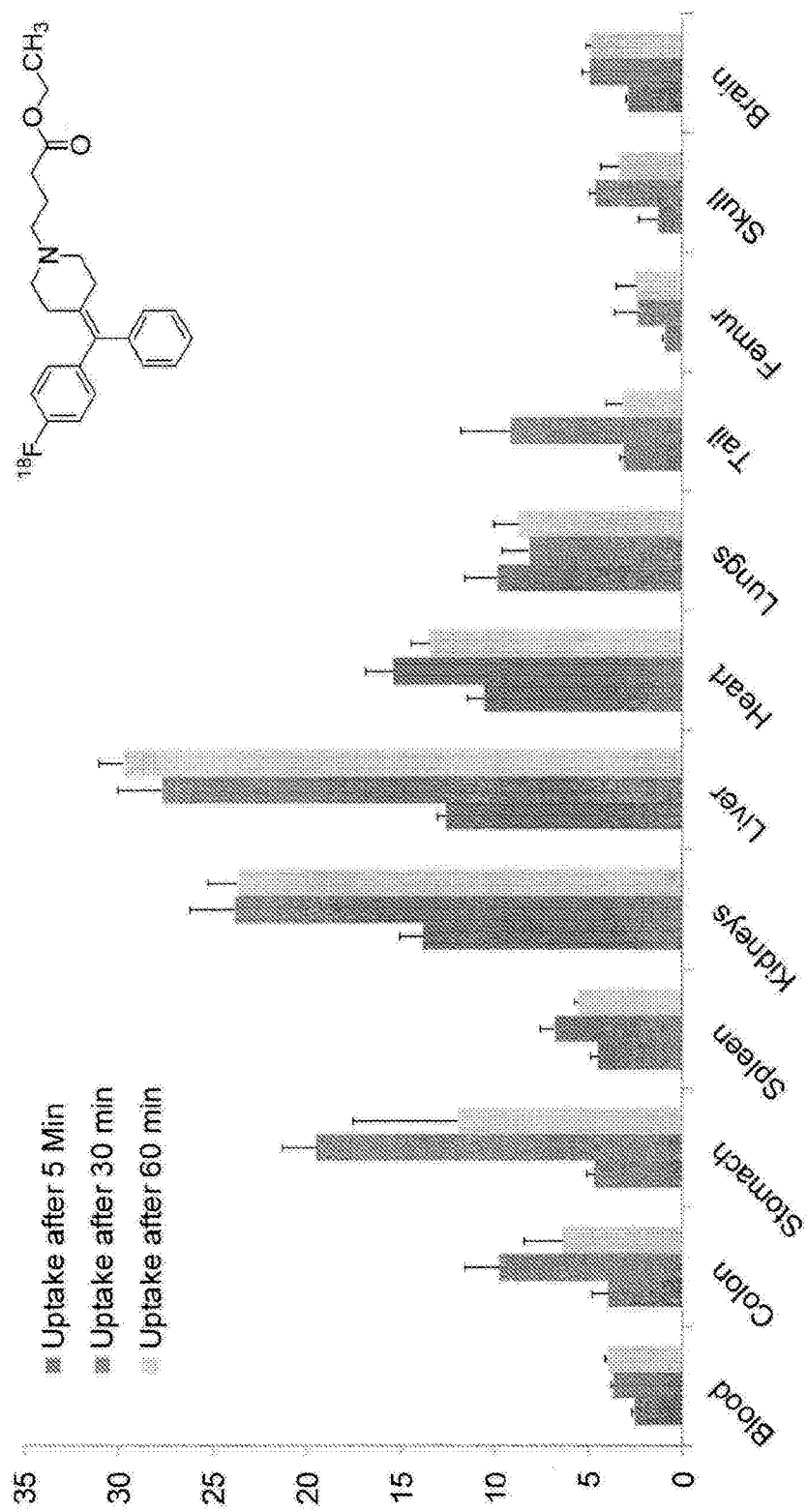
FIG. 10. Biodistribution results 5, 30 and 60 minutes after administration of compound [$^{18}$F]5 after direct labelling of sulfonium salt P5 with fluoride-18.
Figure 11:
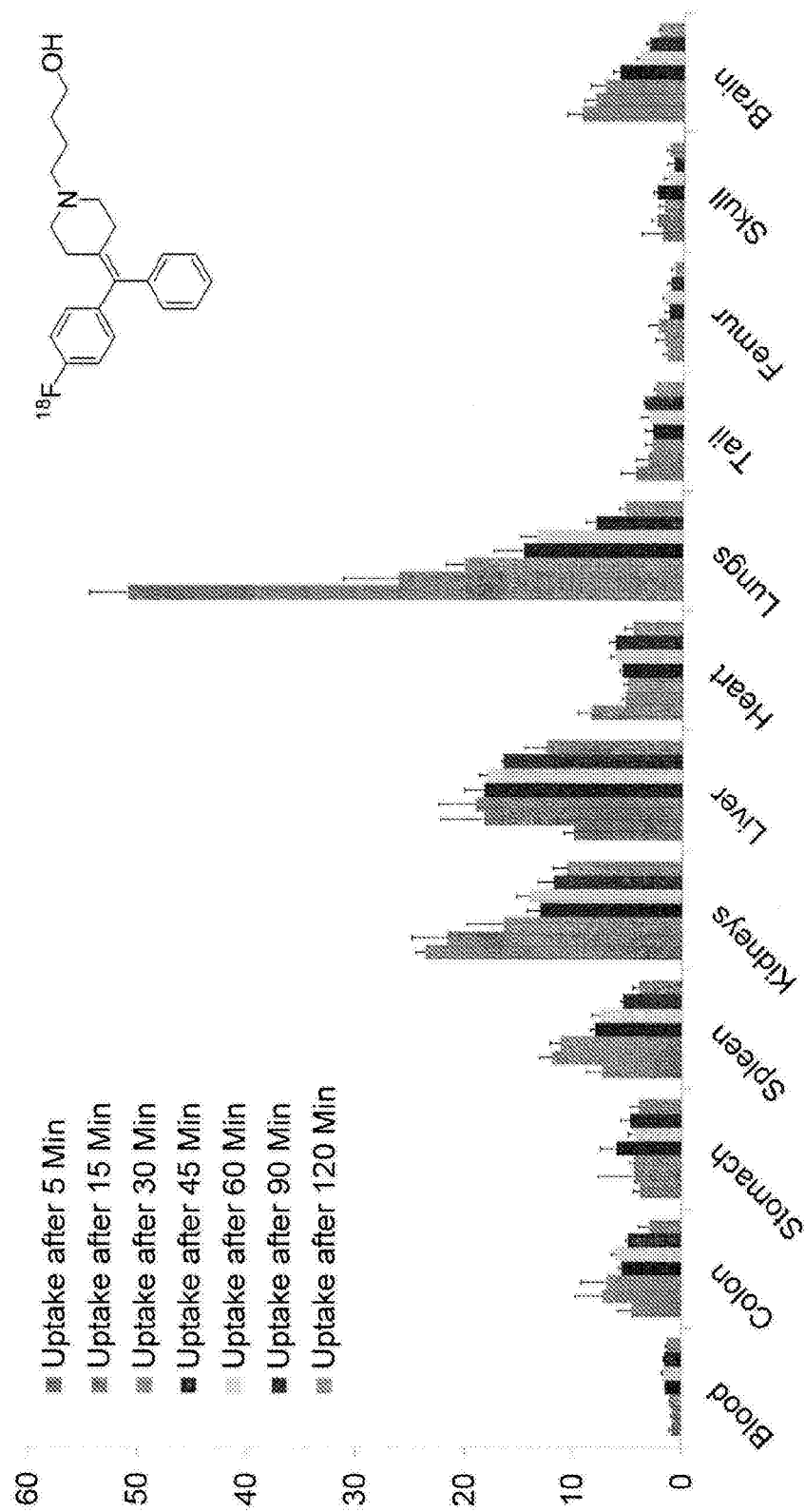
FIG. 11. Biodistribution results 5, 15, 30, 45, 60, 90 and 120 minutes after administration of an $^{18}$F-labelled compound corresponding to compound [$^{18}$F]6.
Figure 12:
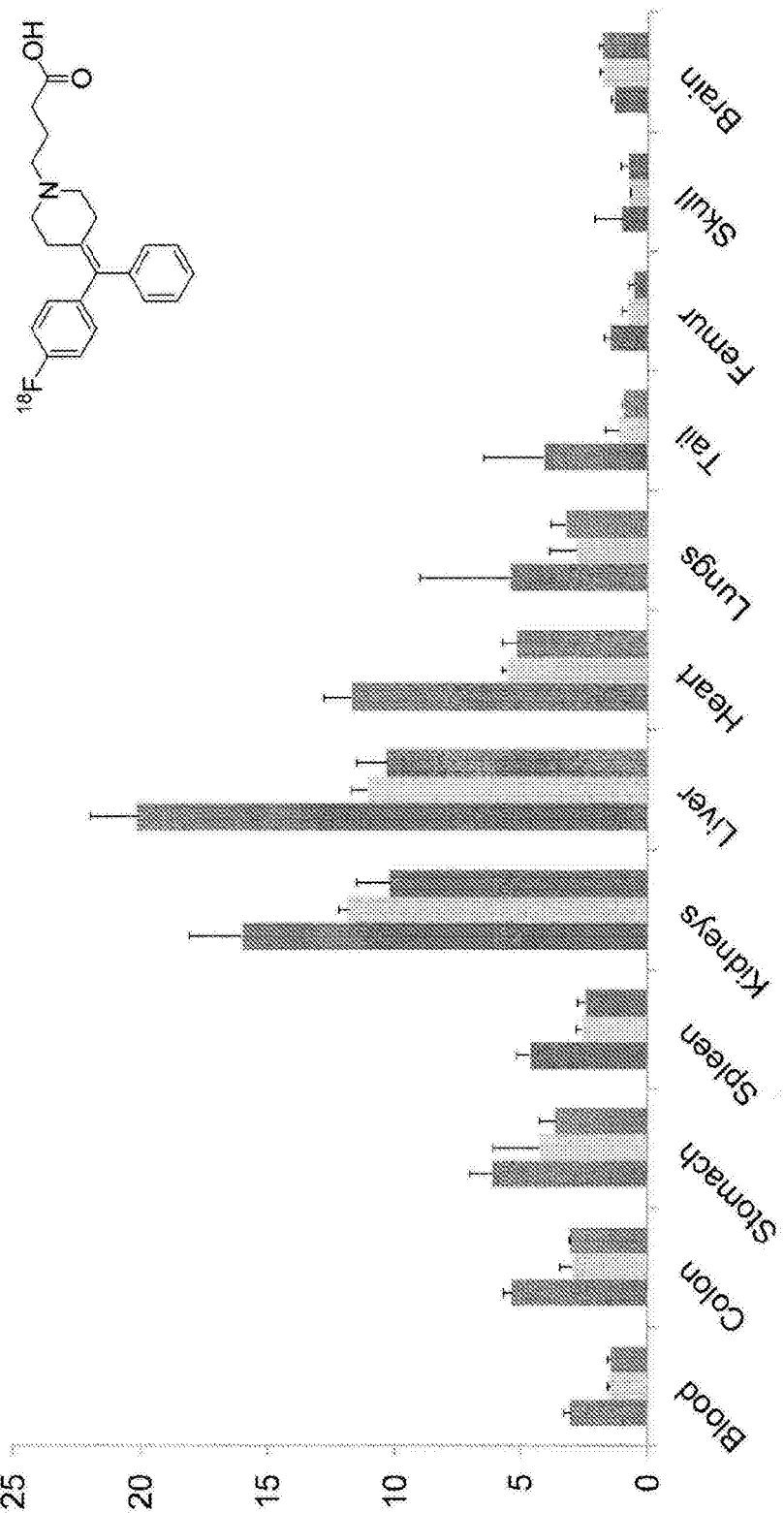
FIG. 12. Biodistribution results 5, 60 and 120 minutes after administration of an $^{18}$F-labelled carboxylate compound corresponding to a compound derived from P5.
Figure 13:
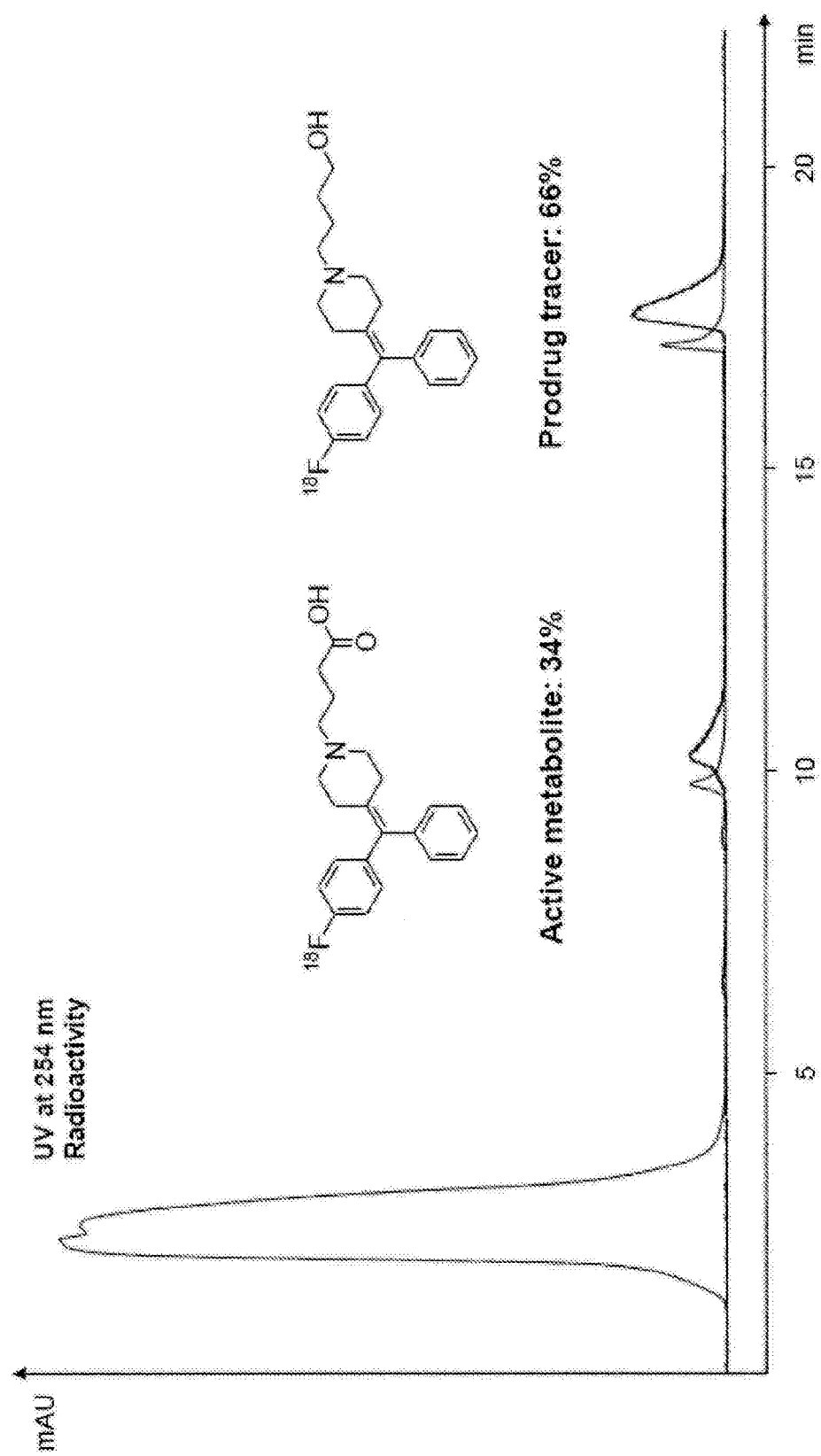
FIG. 13. Brain metabolite analysis 60 minutes after administration of compound [$^{14}$]6.
Figure 14:
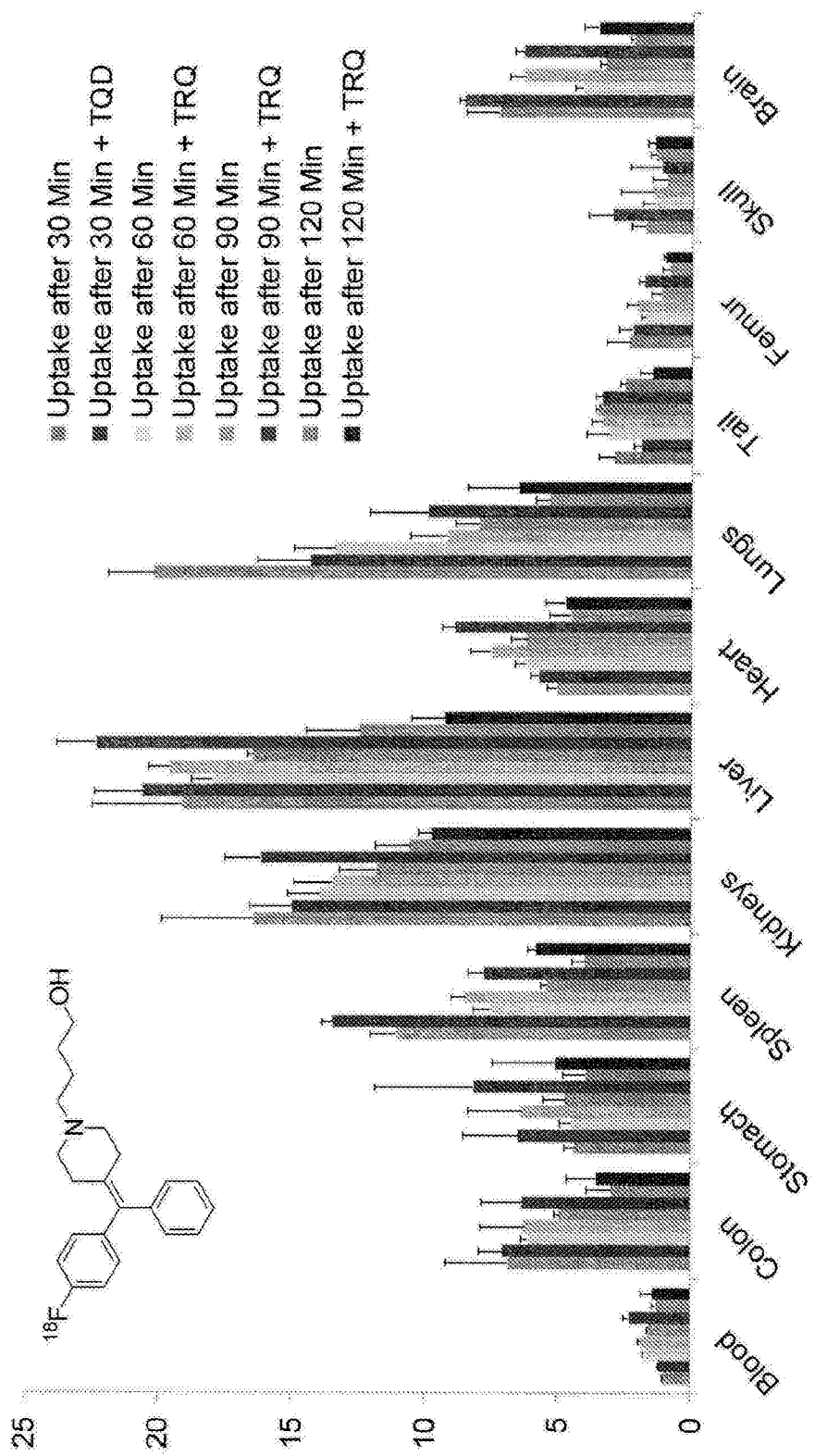
FIG. 14. Biodistribution results 30, 60, 90 and 120 minutes after administration of the compound [$^{18}$F]6, with P-glycoprotein activity inhibited by concomitant administration of the P-glycoprotein inhibitor tariquidar ("+TQD") indicating that the metabolite as shown in FIG. 13 is transported by the efflux pump.
Figure 15:
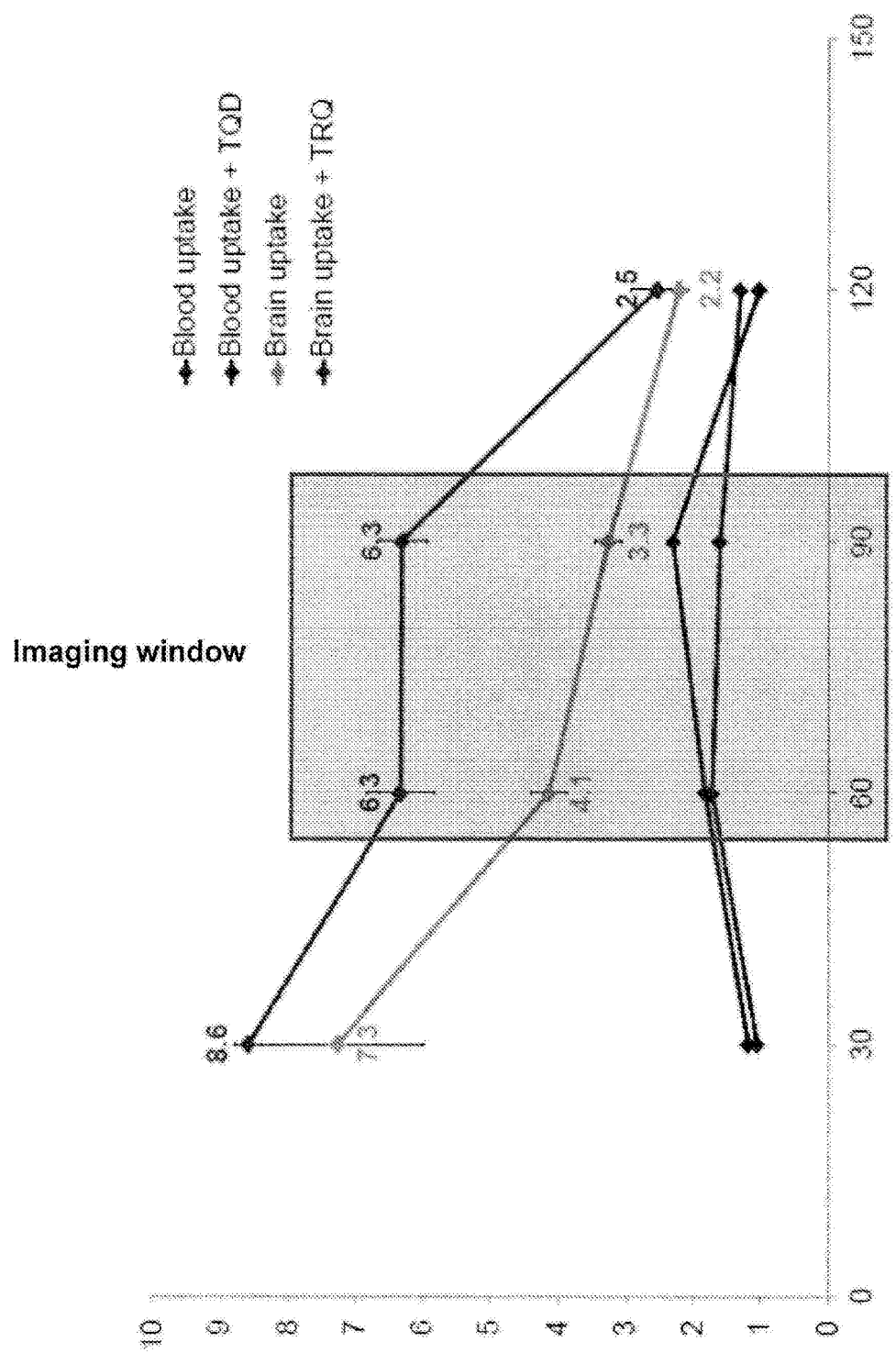
FIG. 15. Blood and brain uptake of compound [$^{18}$F]6 over time, with and without inhibition of P-glycoprotein activity by concomitant administration of TQD. Results exhibit a high brain uptake as well as a good brain to blood ratio suitable for nuclear imaging. The tracer is consistently washed out of the brain by P-glycoprotein. Inhibition of the efflux pump results in a plateau between 60 and 90 minutes after injection, indicating the window for quantitative imaging of the efflux pump. The upper line (from the left most point of the line) relates to 'brain uptake+TQD', the second from top line relates to 'brain uptake', the second from bottom line relates to 'blood uptake+TQD', and the bottom line relates to 'blood uptake'.

Conventional reaction conditions (heating at 110° C.) yielded almost 50% of radioactive product. When the reaction was performed at room temperature ca. 20% conversion was observed. The yield dropped to about 10% under UV irradiation, whereas reactions under light exclusion do not show differences to reactions performed without shielding from electric lighting. Importantly, only the reaction performed at ambient temperature did not show any side products, whilst energy input (heat or UV light) caused the formation of side products. UV chromatograms also showed significant differences; heating clearly led to decomposition of the sulfonium precursor and induced generation of side products. UV-irradiated reactions proceed much cleaner. However, side products most probably resulting from the photolytic cleavage of the precursor can be identified. Neither decomposition nor formation of side products was observed after performing reactions at room temperature, which significantly facilitates purification steps (FIGS. 4-6).

Example 11—Trapping of Fluoride-18 by Sulfonium Salts on Solid Phase Extraction Cartridges (A)—Fluoride Trapping on a Strata® C-18 SPE Column
Precursor compound 4 (2 mg dissolved in 2 ml water containing 5% methanol) was loaded on the preconditioned (5 ml methanol, followed by 10 ml water) SPE column. Fluoride-18 from the target water (59.11 MBq in 1 ml water) was trapped leading to 58.65 MBq of radioactivity on the column. It was subsequently washed with water (2 ml→55.48 MBq), tetrahydrofuran (0.5 ml→48.97 MBq) and dried under a stream of nitrogen for five minutes (→p 40.84 MBq).

(B)—Fluoride Trapping on a Sep-Pak® Light C-18 SPE Cartridge
Triphenylsulfoniumtriflate (1 mg dissolved in 1 ml water containing 10% methanol) was loaded on the preconditioned (5 ml methanol, followed by 10 ml water) SPE cartridge. Fluoride-18 from the target water (20 MBq in 1 ml water) was trapped leading to 15.6 MBq of radioactivity on the cartridge. It was subsequently washed with water (1 ml→14.96 MBq), acetonitrile (0.5 ml→14.25 MBq) and dried under a stream of nitrogen for ten minutes (→12.49 MBq).

Example 12—Application of the Reported Chemistry to the Production of Radiotracers Investigated In Vivo A series of radiolabelled tracers was prepared using the reported chemistry and investigated in vivo (Balb/C or FVB mice) by biodistribution studies and/or metabolite analysis. Examples in FIGS. 7-10 highlight the versatility of the reported chemistry that allows for tracers with a variety of backbone structures and side chains. By deliberately modifying chemical moieties the tracer can be fine-tuned towards up-take in tissues of interest, e.g. brain, heart or lungs. FIGS. 11-15 show the results of the in vivo investigation of a potential pro-drug tracer that was developed to monitor the efflux pump P-glycoprotein at the blood-brain barrier.
Mice:
Female Balb/C mice and FVB mice were obtained from Charles River UK. When used, they were eight to eleven weeks old and weighing approximately 20 g. All biological work was carried out by licensed investigators in accordance with the UK Home office's Animals (Scientific procedures) Act 1986.
Biodistribution Studies:
The respective radiotracer (0.5-1 MBq formulated in a saline solution containing 5% ethanol) was administered intravenously into the tail vein. At designated time points between five and 120 minutes after injection, mice were anesthetized with isoflurane (5% mixed with medical air at a flow of 2 ml/min) and sacrificed by cardiac puncture. The organs of interest (blood, colon, stomach, spleen, kidneys, liver, heart, lungs, tail, femur, skull, and brain) were sampled, weighed, and the radioactivity content was measured by automated gamma counting (Cobra Multi Gamma Model 5010-Packard, UK). Results were normalised to the radioactivity found in 1% of the injected dose per gram bodyweight. All experiments were performed in duplicates or triplicates and analysed using Microsoft Office Excel 2007.
Metabolite Analysis:
Brains were homogenised in saline (0.5 ml) and ethanol (0.5 ml). Samples were deproteinated by adding ethanol (0.5 ml) and subsequent centrifugation (3 min, 13,000 rpm). The resulting supernatant was separated from the pellet, diluted with saline (0.5 ml) and analysed by radio-HPLC, using a Luna® 3 µm C8(2) 100 Å, LC column (30×4.6 mm). The mobile phase consisted of water and methanol containing 0.02% ammonium hydroxide and was used for gradient elution (from 30% of methanol to 90% in 15 min, then 5 minutes at 90%). The flow rate was 1 ml/min and the UV absorbance detector was set at 254 nm. All experiments were performed in triplicates.

The invention claimed is:

1. A sulfonium salt according to formula (I):

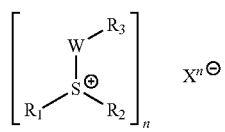

wherein
$R_1$ and $R_2$ are joined together to form, together with the sulfur atom, an optionally substituted dibenzothiophene ring;
W is an optionally substituted aryl group or an optionally substituted heteroaryl group;
$R_3$ is a moiety comprising at least one basic group, wherein the basic group of $R_3$ is a Brønsted base and/or Lewis base and is selected from a primary amine, secondary amine, tertiary amine, amidine, guanidine, enamine, hydrazine, hydrazone, hydroxylamine, imine, an N-containing-heterocyclyl group, and an N-containing-heteroaryl group;
X is an anionic species; and
n is an integer selected from 1 to 5,
wherein W—$R_3$ is a group capable of binding to a biological target and/or is a biologically active agent,
wherein the aryl group of the optionally substituted aryl group of W is a $C_6$-$C_{16}$ aryl group, and
wherein the heteroaryl group of the optionally substituted heteroaryl group of W is a 5-6 membered monocyclic or 8-16 membered fused bicyclic or tricyclic heteroaryl group.

2. A sulfonium salt according to claim 1, wherein W is a $C_6$-$C_{14}$ aryl group.

3. A sulfonium salt according to claim 1, wherein W—$R_3$ is a fragment of a known pharmacologically active agent.

4. A sulfonium salt according to claim 1, wherein X is selected from halide, triflate, mesylate, tosylate, tetrafluoroborate, and hexafluoroantimonate.

5. A method of preparing a sulfonium salt according to claim 1, the method comprising
i) treating a thioether according to formula (II)

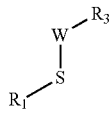

with an acidic compound so as to form an acid-base adduct by virtue of the basic group of $R_3$;
ii) treating the adduct with a compound according to the formula $[(R_2)_2 I]m^+ Z^{m-}$ or formula $[(R_1)(R_2)I]m^+ Z^{m-}$, optionally in the presence of a catalyst,
or where $R_1$ and $R_2$ are joined together to form an optionally substituted sulfur-containing ring in formula (I), treating an adduct of formula (II) formed in step (i) in which $R_1$ contains at least one unsaturated bond, with an acid or electrophilic species so as to cause formation of the optionally substituted sulfur-containing ring; and
iii) recovering the product sulfonium salt,
wherein $R_1$, $R_2$, W, and $R_3$ are as defined in claim 1, Z is an anionic species, and m is an integer selected from 1 to 5.

6. A method according to claim 5, wherein the acidic compound is a protic acid.

7. A method according to claim 6, wherein the acidic compound is selected from sulfuric acid, fluorosulfuric acid, nitric acid, phosphoric acid, fluoroantimonic acid, fluoroboric acid, hexafluorophosphoric acid, chromic acid, boric acid, methanesulfonic acid, ethanesulfonic acid, benzenesulfonic acid, p-toluenesulfonic acid, trifluoromethanesulfonic acid, trifluoroacetic acid, acetic acid, citric acid, formic acid, hydrogen chloride, hydrogen bromide, and hydrogen iodide.

8. A method according to claim 5, wherein the catalyst is a transition metal coordination complex.

9. A method according to claim 8, wherein the catalyst is a copper (II) complex.

10. A method of preparing a compound according to formula (III):

the method comprising
i) treating a sulfonium salt according to claim 1 with a species capable of generating a nucleophile Y, optionally in the presence of a base and/or chelating agent; and
ii) recovering the compound according to formula (III), wherein $R_3$ and W are as defined in claim 1.

11. A method according to claim 10, wherein the base is selected from sodium hydroxide, lithium hydroxide, potassium hydroxide, sodium hydrogen carbonate, potassium hydrogen carbonate, sodium carbonate, potassium carbonate, and caesium carbonate.

12. A method according to claim 10, wherein the chelating agent is a cryptand or a crown ether.

13. A method according to claim 12, wherein the chelating agent is selected from 21-cryptand, 211-cryptand, 221-cryptand, 222-cryptand, 222B-cryptand, 12-crown-4, 15-crown-5, 18-crown-6, dibenzo-18-crown-6, and diaza-18-crown-6.

14. A method according to claim 10, wherein the nucleophile is selected from a hydrocarbon species capable of forming a carbon anion, an amine, an amide, an alkoxy group, a phenolate, a thiolate, a thiophenolate, a cyanate, a thiocyanate, and a halide.

15. A method according to claim 14, wherein the nucleophile is a halide.

16. A method according to claim 10, wherein the sulfonium salt is linked to a surface of a solid phase adsorbent.

17. A method according to claim 16, wherein the solid phase adsorbent is a reversed phase adsorbent.

18. A method according to claim 16, wherein the solid phase adsorbent is presented in conjunction with a column or cartridge.

19. A halogenated compound obtainable by the method of claim 10.

20. A solid phase adsorbent comprising a sulfonium salt according to claim 1.

21. A solid phase adsorbent according to claim 20, wherein the solid phase adsorbent is presented in conjunction with a column or cartridge.

* * * * *